US012784223B2

(12) United States Patent
Kobayashi et al.

(10) Patent No.: US 12,784,223 B2
(45) Date of Patent: Nov. 3, 2026

(54) SURGERY DETAILS EVALUATION SYSTEM, SURGERY DETAILS EVALUATION METHOD, AND COMPUTER PROGRAM

(71) Applicant: Anaut Inc., Tokyo (JP)

(72) Inventors: Nao Kobayashi, Kanagawa (JP); Yuta Kumazu, Kanagawa (JP); Seigo Senya, Kanagawa (JP)

(73) Assignee: Anaut Inc., Tokyo (JP)

( * ) Notice: Subject to any disclaimer, the term of this patent is extended or adjusted under 35 U.S.C. 154(b) by 375 days.

(21) Appl. No.: 18/547,520

(22) PCT Filed: Feb. 24, 2022

(86) PCT No.: PCT/JP2022/007707
§ 371 (c)(1),
(2) Date: Aug. 23, 2023

(87) PCT Pub. No.: WO2022/181714
PCT Pub. Date: Sep. 1, 2022

(65) Prior Publication Data

US 2024/0135542 A1 Apr. 25, 2024
US 2024/0233126 A9 Jul. 11, 2024

(30) Foreign Application Priority Data

Feb. 24, 2021 (JP) ................................ 2021-027782

(51) Int. Cl.
*G06K 9/00* (2022.01)
*G06T 7/00* (2017.01)
*G16H 30/20* (2018.01)

(52) U.S. Cl.
CPC .......... *G06T 7/0016* (2013.01); *G16H 30/20* (2018.01); *G06T 2207/30004* (2013.01); *G06T 2207/30196* (2013.01); *G06T 2207/30241* (2013.01)

(58) Field of Classification Search
None
See application file for complete search history.

(56) References Cited

U.S. PATENT DOCUMENTS

2020/0268457 A1 8/2020 Wolf et al.
2020/0367974 A1 11/2020 Khalid et al.
(Continued)

FOREIGN PATENT DOCUMENTS

JP 2017-047022 A 3/2017
JP 2019-500921 A 1/2019
(Continued)

OTHER PUBLICATIONS ( No. 5 ) "The first patient weighed 130 kg. Decided to take on the challenge of difficult surgery" Jiji Press, Ltd.Published on May 17, 2018, URL: https://medical.jiji.com/column/116?page=2.
(Continued)

*Primary Examiner* — Wei Wen Yang
(74) *Attorney, Agent, or Firm* — SoCal IP Law Group LLP; Mark Andrew Goldstein

(57) ABSTRACT

The purpose of the present invention is to make it possible to objectively evaluate the details of an actual surgery. In the present invention, a surgery details evaluation system 1 evaluates the details of a surgery carried out by a surgeon, the surgery details evaluation system 1 comprising: an acquisition means 11 for acquiring a surgical image, which is a captured image of the body of a patient undergoing surgery carried out by a surgeon; an analysis unit 12 for analyzing body information indicating the state of the body and/or instrument information indicating the state of an instrument being operated by the surgeon in the surgical image; and an evaluation unit 14 for evaluating the details of the surgery being carried out by the surgeon, the evaluation
(Continued)

being performed on the basis of the body information and/or the instrument information analyzed by the analysis unit 12.

15 Claims, 20 Drawing Sheets

(56) References Cited

U.S. PATENT DOCUMENTS

| | | | | |
|---|---|---|---|---|
| 2021/0012868 | A1* | 1/2021 | Wolf | G11B 27/10 |
| 2021/0142487 | A1 | 5/2021 | Xu et al. | |
| 2022/0233241 | A1* | 7/2022 | Shelton, IV | A61B 5/7405 |

FOREIGN PATENT DOCUMENTS

| | | | |
|---|---|---|---|
| JP | 2020-071418 | A | 5/2020 |
| JP | 2021-099789 | A | 7/2021 |
| KR | 10-2180921 | B1 | 11/2020 |
| WO | 2017/075541 | A1 | 5/2017 |
| WO | 2019/133128 | A1 | 7/2019 |
| WO | 2019/226182 | A1 | 11/2019 |
| WO | 2022/181714 | A1 | 9/2022 |

OTHER PUBLICATIONS

World Intellectual Property Organization, International Search Report for Intellectual No. PCT/JP2022/007707, mail date May 24, 2022, 6 pages.

European Intellectual Property Office, Office Action for EP Patent Application No. EP22759749.9, mail date Apr. 23, 2025.

European Intellectual Property Office, Office Action for European Patent Application No. EP22759749.9, mail date Oct. 27, 2025, 8 total pages.

* cited by examiner

D3 D4

D3 D4

LEAN TYPE LOW DIFFICULTY LEVEL

BLOOD VESSEL

OBESE TYPE HIGH DIFFICULTY LEVEL

ADHESION

SURGERY DETAILS EVALUATION SYSTEM, SURGERY DETAILS EVALUATION METHOD, AND COMPUTER PROGRAM

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by anyone of the patent disclosure as it appears in the Patent and Trademark Office patent files or records, but otherwise reserves all copyright and trade dress rights whatsoever.

RELATED APPLICATION INFORMATION

This patent claims priority from International PCT Patent Application No. PCT/JP2022/007707, filed Feb. 24, 2022 entitled, SURGERY DETAILS EVALUATION SYSTEM, SURGERY DETAILS EVALUATION METHOD, AND COMPUTER PROGRAM, which claims priority to Japanese Application No. 2021-027782, filed Feb. 24, 2021, all of which are incorporated herein by reference in their entirety.

TECHNICAL FIELD

The present invention relates to a surgical content evaluation method and a computer program for evaluating the content of surgery performed by a surgeon.

BACKGROUND ART

Conventionally, it has been known that the burden on the body of a patient largely varies depending on the technique of surgery of a surgeon and how the surgery proceeds. Therefore, surgeons are required to improve surgery skill.

For example, Patent Document 1 discloses a surgical simulation with a computer simulator, in which a simulation motion computing device executes the surgical simulation including: a first process of loading and executing an education scenario sequence from a storage device at the start of the surgical simulation; a second process of storing simulated surgical instrument information during a simulation calculated by the simulated motion computing device and simulation model data information in the storage device; and a third process of performing evaluation according to an evaluation item based on the simulated surgical instrument information and simulation model data information stored in the storage device at the end of the simulation.

Patent Document 1: Japanese Unexamined Patent Application, Publication No. 2020-71418.

DISCLOSURE OF THE INVENTION

Problems to be Solved by the Invention

However, in the surgical simulation of Patent Document 1, although the technology in the simulated surgical simulation can be evaluated, the contents of actual surgery cannot be evaluated. To improve the skill of surgery, it is indispensable to objectively evaluate the contents of actual surgery. By confirming the objective evaluation of the actual surgical contents, the surgeon clarifies the learning and improvement points, and by eliminating the learning and improvement points, the skill of the surgery is further improved.

It is an object of the present invention to provide a surgical content evaluation system, a surgical content evaluation method, and a computer program capable of objectively evaluating the content of an actual surgery. Means for Solving the Problems (1) A surgical content evaluation system for evaluating a content of surgery performed by a surgeon, the system including: an acquisition unit that acquires a surgical image, which is a captured image of a body of a patient on which the surgery is performed by the surgeon; an analysis unit that analyzes, in the surgical image, body information indicating a state of the body and/or instrument information indicating a state of an instrument operated by the surgeon; and an evaluation unit that evaluates the content of the surgery performed by the surgeon based on the body information and/or the instrument information analyzed by the analysis unit.

In the invention of (1), the surgical content evaluation system includes the acquisition unit, the analysis unit, and the evaluation unit, and evaluates the content of the surgery performed by the surgeon. The acquisition unit acquires a surgical image, which is a captured image of the body of the patient on which the surgery is performed by the surgeon. The analysis unit analyzes the body information indicating the state of the body and/or the instrument information indicating the state of the instrument being operated by the surgeon in the surgical image. The evaluation unit evaluates the contents of the surgery performed by the surgeon based on the body information and/or the instrument information analyzed by the analysis unit.

According to the invention of (1), since the contents of the surgery performed by the surgeon are evaluated based on the body information indicating the state of the body and/or the instrument information indicating the state of the instrument operated by the surgeon in the surgical image acquired by image-capturing the body of the patient on which the surgery is performed by the surgeon, it is possible to objectively evaluate the contents of the actual surgery. Accordingly, it is possible to provide a surgical content evaluation system capable of objectively evaluating the content of an actual surgery.

(2) The surgical content evaluation system according to (1), in which the analysis unit analyzes a specific region in the surgical image, and the evaluation unit evaluates that, when the specific region in the surgical image has exceeded a predetermined threshold, a body fluid has flowed out or an organ has been damaged.

Here, for example, in a case in which an organ is damaged, in a surgical image, when bleeding occurs, a blood region expands, when bile flows out, a bile region expands, and when an organ is damaged by an electric scalpel or the like, a cauterized region such as white or black expands. Such outflow of body fluid and organ damage are important as evaluation targets of the contents of surgery in consideration of the influence on the body of the patient.

According to the invention of (2), for example, it is possible to objectively evaluate the outflow of the body fluid or the organ damage, which is an important evaluation target, by setting a region that expands when the outflow of the body fluid or the organ damage occurs as a specific region, determining whether or not the specific region has exceeded a predetermined threshold, and evaluating that, when the specific region in the surgical image has exceeded a predetermined threshold, a body fluid has flowed out or an organ has been damaged.

(3) The surgical content evaluation system according to (1) or (2), in which the analysis unit analyzes the instrument information including information relating to the instrument, and the evaluation unit evaluates an operation performance of the instrument in the surgery based on the information relating to the instrument.

Here, if there is a wasteful movement (for example, the instrument does not move along the shortest distance to the treatment site) in the operation performance of the instrument during surgery, the surgery time is prolonged and the burden on the body of the patient increases. In addition, in a case where the operation performance of the instrument is inappropriate in surgery (e.g., in a case where the orientation of the instrument is inappropriate), the possibility of organ damage caused by the instrument increases. Therefore, in consideration of reducing the burden on the body of the patient during surgery, the operation performance of the instrument is important as an evaluation target of the contents of surgery.

According to the invention of (3), by evaluating the operation performance of the instrument in the surgery based on the information relating to the instrument included in the instrument information, it is possible to objectively evaluate the operation performance of the instrument not only from the result of the sensation of the operator or the result of no damage to the organ.

(4) The surgical content evaluation system according to any one of (1) to (3), in which the analysis unit analyzes the body information including information relating to an anatomical structure of the body, and analyzes the body information and/or the instrument information including information relating to a position of the instrument with respect to the anatomical structure, and the evaluation unit evaluates an operation performance of the instrument with respect to the anatomical structure in the surgery based on the information relating to the position of the instrument with respect to the anatomical structure.

Here, for example, when the affected part in the visceral is resected, it is necessary to separate the affected part from other organs. In this case, it is necessary to appropriately apply an electric scalpel, which is an example of the instrument, to a connective tissue, which is an example of the anatomical structure connecting the affected part and another organ. If the position of the electric scalpel with respect to the connective tissue is not appropriate, the electric scalpel may touch other organs and damage other organs. For this reason, the position of the instrument with respect to the anatomical structure is important as an evaluation target of a factor that leads to mistake in surgery.

According to the invention of (4), by evaluating the operation performance of the instrument with respect to the anatomical structure in the surgery based on the information relating to the position of the instrument with respect to the anatomical structure, it is possible to objectively evaluate the operation performance of the instrument with respect to the anatomical structure not only from the result of the sensation of the operator or the result of no damage to the organ, but also from a possibility of leading to mistake such as organ damage.

(5) The surgical content evaluation system according to any one of (1) to (4), in which the analysis unit analyzes, in the surgical image of the surgery including a plurality of steps, each of the plurality of steps, the surgical content evaluation system further includes a time measurement unit that measures an inter-step period of time, which is a period of time from one step of the plurality of steps to a next other step of the plurality of steps, and the evaluation unit evaluates a surgical skill for the one step of the plurality of steps, based on the inter-step period measured by the time measurement unit.

Here, the surgery includes a plurality of steps, and since the technical difficulty level and the influence on the body of the patient are different for each step, it is necessary to evaluate the contents of the surgery for each step. Therefore, the inter-step period of time, which is the time from one step to the next step, is important as an evaluation target when the contents of the surgery are examined for each step.

According to the invention of (5), since the surgical skill is evaluated based on the inter-step period of time which is the time from one step to the next step, it is possible to objectively evaluate not only the time of the entire surgery, but also the surgical skill of the operator for each step.

(6) A method executed by a surgical content evaluation system for evaluating a content of surgery performed by a surgeon, the method including the steps of: acquiring a surgical image, which is a captured image of a body of a patient on which the surgery is performed by the surgeon; analyzing, in the surgical image, body information indicating a state of the body and/or instrument information indicating a state of an instrument operated by the surgeon; and evaluating the content of the surgery performed by the surgeon based on the body information and/or the instrument information.

(7) A program that causes a surgical content evaluation system for evaluating a content of surgery performed by a surgeon to function as: an acquisition unit that acquires a surgical image, which is a captured image of a body of a patient on which the surgery is performed by the surgeon; an analysis unit that analyzes, in the surgical image, body information indicating a state of the body and/or instrument information indicating a state of an instrument operated by the surgeon; and an evaluation unit that evaluates the content of the surgery performed by the surgeon based on the body information and/or the instrument information analyzed by the analysis unit.

According to the invention of (6) and (7), it is possible to achieve the same advantageous operational effect as the invention of (1).

(8) A surgical content evaluation system for evaluating a content of surgery performed by a surgeon, the system including: an acquisition unit that acquires a surgical image, which is a captured image of a body of a patient on which the surgery is performed by the surgeon; an analysis unit that analyzes, in the surgical image, body information indicating a state of the body; and an evaluation unit that evaluates the content of the surgery performed by the surgeon based on the body information analyzed by the analysis unit.

According to the invention of (8), since the contents of the surgery performed by the surgeon are evaluated based on the body information indicating the state of the body in the surgical image acquired by image-capturing the body of the patient on which the surgery is performed by the surgeon, it is possible to objectively evaluate the contents of the actual surgery. Accordingly, it is possible to provide a surgical content evaluation system capable of objectively evaluating the content of an actual surgery.

(9) The surgical content evaluation system according to (8), in which the analysis unit calculates a recognition degree indicating a degree of recognition of the body information in the surgical image, and the evaluation unit evaluates the content of the surgery performed by the surgeon according to the recognition degree.

According to the invention of (9), the contents of the surgery performed by the surgeon can be evaluated according to the recognition degree indicating the degree of recognition of the body information in the surgical image.

(10) The surgical content evaluation system according to (9), in which the analysis unit calculates a confidence degree indicating a degree of confidence of an analysis result of the body information, and calculates the recognition degree based on the confidence degree.

According to the invention of (10), the analysis unit can calculate the recognition degree based on the confidence degree indicating the degree of confidence of the analysis result of the body information.

(11) The surgical content evaluation system according to (9) or (10), in which the evaluation unit evaluates the content of surgery performed by the surgeon according to a temporal change of the recognition degree.

According to the invention of (11), it is possible to evaluate the contents of the surgery performed by the surgeon according to the temporal change of the recognition degree.

(12) The surgical content evaluation system according to any one of (8) to (11), in which the evaluation unit evaluates a difficulty level of surgery according to information relating to an anatomical structure of the body included in the body information.

According to the invention of (12), it is possible to evaluate the difficulty level of the surgery according to the information relating to the anatomical structure of the body included in the body information.

(13) The surgical content evaluation system according to any one of (8) to (12), in which the analysis unit analyzes a trajectory of a distal end position of an instrument operated by the surgeon, and the evaluation unit evaluates an operation performance of the instrument in the surgery based on the trajectory.

According to the invention of (13), it is possible to evaluate the operation performance of the instrument in the surgery based on the trajectory of the distal end position of the instrument operated by the surgeon.

(14) The surgical content evaluation system according to any one of (8) to (13), in which the analysis unit analyzes a positional relationship between a point of action, which is a portion of the instrument operated by the surgeon in contact with the anatomical structure, and a portion of the anatomical structure in contact with the instrument, and the evaluation unit evaluates the operation performance of the instrument in the surgery based on the positional relationship.

According to the invention of (14), it is possible to evaluate the operation performance of the instrument in the surgery based on the positional relationship between the point of action which is the portion of the instrument being operated by the surgeon in contact with the anatomical structure and the portion of the anatomical structure in contact with the instrument.

(15) The surgical content evaluation system according to any one of (9) to (14), in which the acquisition unit acquires a plurality of surgical images continuously in a time series, and the evaluation unit identifies, among the plurality of surgical images, a surgical image having a recognition degree with respect to information relating to a specific anatomical structure included in the body information that is determined to be equal to or greater than a specific threshold in the analysis unit.

According to the invention of (15), among the plurality of surgical images continuously in a time series, it is possible to identify a surgical image having a recognition degree with respect to information relating to a specific anatomical structure included in body information that is determined to be equal to or greater than a specific threshold.

(16) A method executed by a surgical content evaluation system for evaluating a content of surgery performed by a surgeon, the method including the steps of: acquiring a surgical image, which is a captured image of a body of a patient on which the surgery is performed by the surgeon; analyzing, in the surgical image, body information indicating a state of the body; and evaluating the content of the surgery performed by the surgeon based on the body information analyzed by the analysis unit.

(17) A program that causes a surgical content evaluation system for evaluating a content of surgery performed by a surgeon to function as: an acquisition unit that acquires a surgical image, which is a captured image of a body of a patient on which the surgery is performed by the surgeon; an analysis unit that analyzes, in the surgical image, body information indicating a state of the body; and an evaluation unit that evaluates the content of the surgery performed by the surgeon based on the body information analyzed by the analysis unit.

According to the invention of (16) (17), it is possible to achieve the same advantageous operational effect as the invention of (8).

Effects of the Invention

According to the present invention, it is possible to provide a surgical content evaluation system, a surgical content evaluation method, and a computer program capable of objectively evaluating the content of an actual surgery.

BRIEF DESCRIPTION OF THE DRAWINGS

FIG. 4 provides views illustrating processing of an evaluation unit in the surgical content evaluation system according to the embodiment of the present invention, in which

FIG. 6 provides views illustrating processing performed by the evaluation unit in the surgical content evaluation system according to the embodiment of the present invention, in which

FIG. 7 provides views illustrating processing of an evaluation unit in the surgical content evaluation system according to the embodiment of the present invention, in which

FIG. 16 provides views illustrating processing of an evaluation unit in the surgical content evaluation system according to the embodiment of the present invention;

PREFERRED MODE FOR CARRYING OUT THE INVENTION

Figure 1:
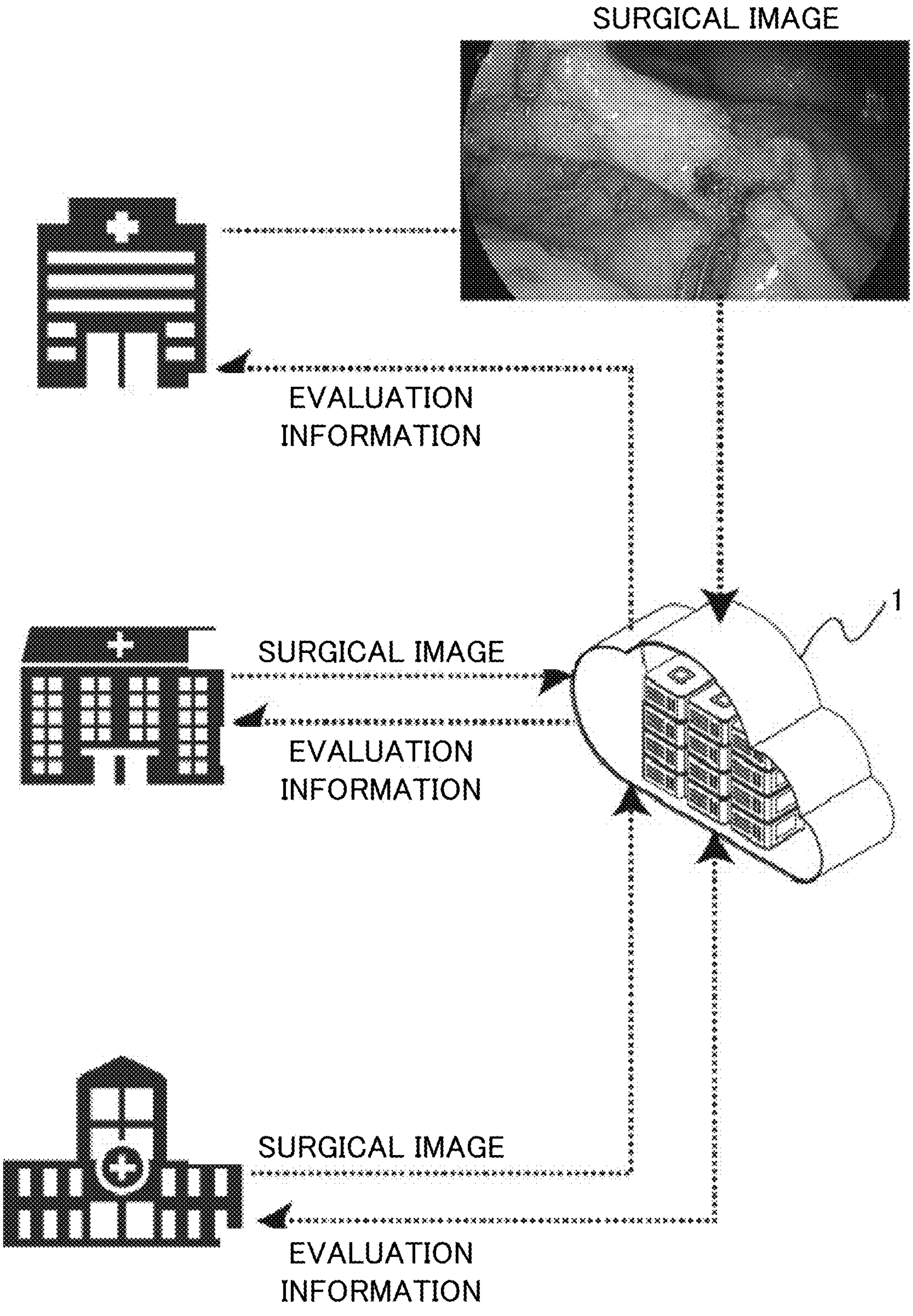
FIG. 1 is a diagram illustrating an outline of a surgical content evaluation system according to an embodiment of the present invention.

Embodiments of the present invention will now be described in detail with reference to the accompanying drawings. In the following drawings, like elements are denoted by like reference numerals throughout the description of the embodiments.

Basic Concept/Basic Configuration

FIG. 1 is a diagram illustrating an outline of a surgical content evaluation system according to an embodiment of the present invention. The surgical content evaluation system 1 evaluates the content of the surgery performed by the surgeon.

The surgical content evaluation system 1 acquires a surgical image, which is an image obtained by imaging a state of surgery by a surgeon in a medical institution (for example, an institution in which surgery is performed by a surgeon such as a hospital). In the surgical image, the body of a patient on which a surgery or surgical operation is performed and the state of an instrument during the operation (for example, forceps and energy devices such as electric scissors, electric scalpels, ultrasonic coagulation incision devices) operated by a surgeon, an assistant, or the like are captured. The surgical image may be a moving image or, for example, a still image continuously captured in time series. Further, in the present embodiment, the surgical image is an image captured by a camera inserted from the access port in an endoscopic surgery. However, the surgical image is not limited thereto, and may be, for example, an image captured by a surgery support robot or an image captured from above the patient as long as the body of the patient on which surgery is performed and an instrument operated by the surgeon or the assistant during the surgery are captured in the surgical image.

The surgical content evaluation system 1 analyzes body information indicating a state of a body and/or instrument information indicating a state of an instrument operated by a surgeon in a surgical image using AI (Artificial Intelligence).

Then, the surgical content evaluation system 1 evaluates the content of the surgery performed by the surgeon using AI based on the body information and/or the instrument information analyzed by the analysis unit, and transmits evaluation information indicating an evaluation result to, for example, a terminal of a medical institution in which the surgeon can confirm the evaluation result.

According to the surgical content evaluation system 1, since the contents of the surgery performed by the surgeon are evaluated by AI based on the body information indicating the state of the body and/or the instrument information indicating the state of the instrument operated by the surgeon in the surgical image obtained by imaging the body of the patient on which the surgery is operated by the surgeon, it is possible to objectively evaluate the contents of the actual surgery. Therefore, it is possible to objectively evaluate the contents of the actual surgery.

Functional Configuration

Figure 2:
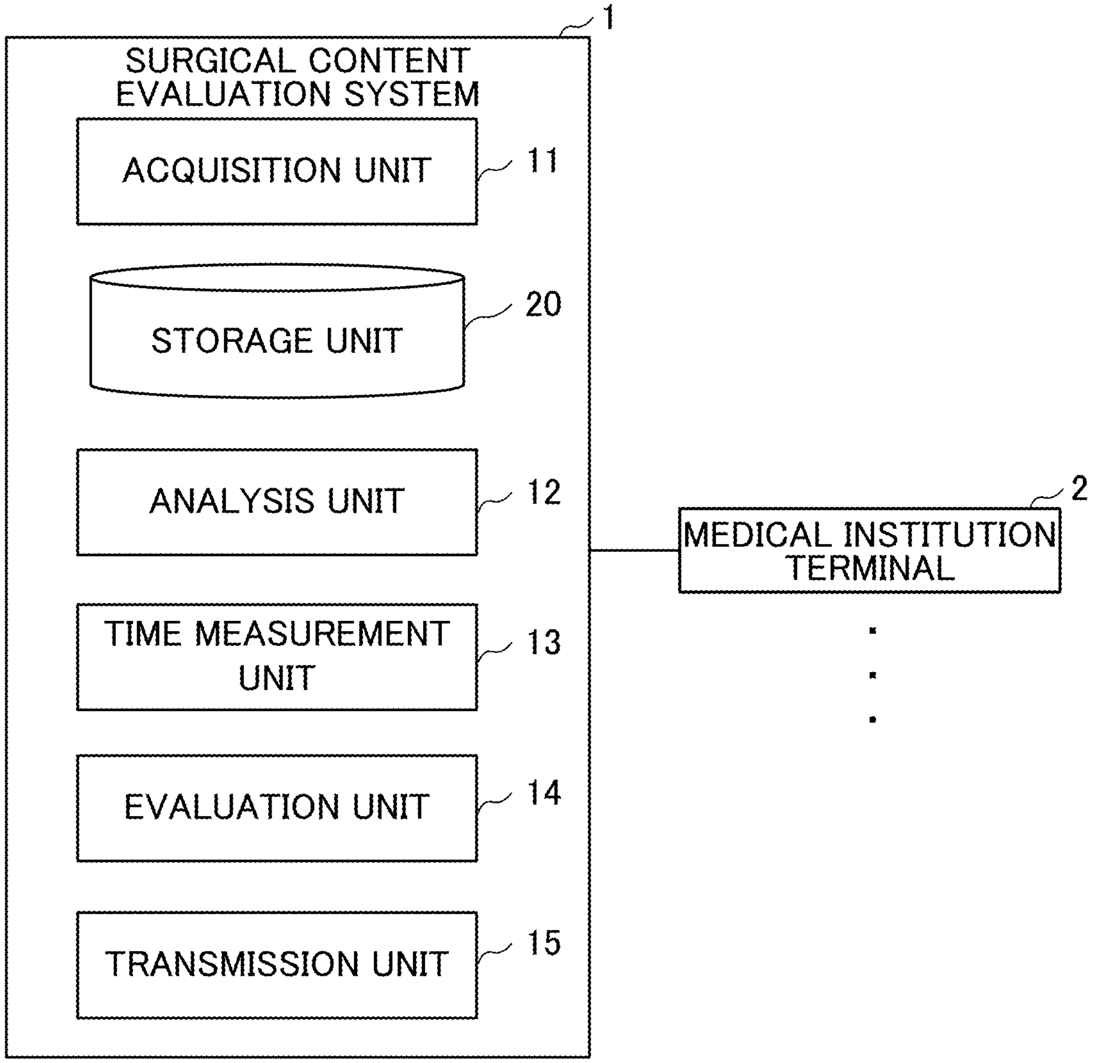
FIG. 2 is a diagram showing a functional configuration of a surgical content evaluation system according to the embodiment of the present invention.

FIG. 2 is a diagram showing a functional configuration of the surgical content evaluation system according to the embodiment of the present invention. The surgical content evaluation system 1 is connected to a plurality of medical institution terminals 2 via a network, and includes an acquisition unit 11, an analysis unit 12, a time measurement unit 13, an evaluation unit 14, a transmission unit 15, and a storage unit 20.

In the present embodiment, the medical institution terminal 2 may be a terminal managed by a medical institution, or may be a terminal installed in a medical institution, managed by an operator of the surgical content evaluation system 1, capable of transmitting a surgical image captured by an imaging unit (for example, a camera) for capturing a surgical image to the surgical content evaluation system 1, and receiving evaluation information from the surgical content evaluation system 1.

The acquisition unit 11 acquires a surgical image, which is a captured image of the body of the patient on which the surgery by the surgeon is performed. The acquisition unit 11 may receive a surgical image from the medical institution terminal 2, may receive a surgical image from another device (e.g., a server that accumulates surgical images), or may read a surgical image stored in advance in the storage unit 20 from the storage unit 20. Further, the acquisition unit 11 may receive audio data during surgery corresponding to the surgical image. In addition to the result of analysis of the surgical image, based on such audio data, for example, the state of communication between the operator and the assistant, the enthusiasm of the operator, the mental state of the operator such as impatience, and the guidance of the operator to the assistant may be evaluated.

Further, when instrument information (e.g., positional information detected in time series of surgery) indicating the state of the instrument operated by the surgeon is detected by various sensors (e.g., a gyro sensor) included in the instrument, the acquisition unit 11 may acquire such instrument information and store the instrument information in the storage unit 20 in association with a corresponding surgical image.

The storage unit 20 stores a surgical image, learned information for analysis for use in the analysis unit 12 for performing analysis to be described later, and learned information for evaluation for use in the evaluation unit 14 for performing evaluation to be described later.

The learned information for analysis is generated by causing AI to learn a plurality of surgical images performed in the past. The learned information for analysis includes: a step recognition model for recognizing a plurality of steps constituting a surgery; a specific region analysis model for analyzing a specific region in the surgical image (for example, a region identified as a body fluid (e.g., a red region formed by outflow of blood, a yellow region formed by outflow of bile, or the like), a region where an organ is burned, or the like); an anatomical structure identification model for identifying an anatomical structure (an organ, a blood vessel, a fat, a connective tissue, or the like) of a patient; and an instrument identification model for identifying each instrument (for example, forceps, energy devices such as electric scissors, electric scalpels, and the like) used by a surgeon (an operator, an assistant, or the like). It is desirable that the learned information for analysis can change the detection threshold at the time of analysis.

The learned information for evaluation is generated by causing AI to learn a plurality of surgical images performed in the past. The learned information for evaluation includes a specific region threshold model that shows a predetermined threshold for a size of a specific region in a surgical image, an anatomical structure/instrument state determination model for determining the state of an anatomical structure for each of a plurality of steps constituting the surgery and the state of the instrument (the type of the instrument, the position of the instrument, the orientation of the instrument, and the like). It is desirable for the learned information for analysis to be able to change the detection threshold at the time of determination.

The learned information for analysis and the learned information for evaluation are generated by any learning method such as publicly known machine learning, deep learning, and reinforced learning, and are stored in the storage unit 20 in advance. The learned information for analysis and the learned information for evaluation may be generated by the surgical content evaluation system 1, or may be generated by an external device and stored in the storage unit 20.

The analysis unit 12 analyzes body information indicating the state of the body and/or instrument information indicating the state of the instrument operated by the surgeon in the surgical image acquired by the acquisition unit 11.

Specifically, the analysis unit 12 compares the surgical image acquired by the acquisition unit 11 with the step recognition model stored in the storage unit 20, and analyzes which of the plurality of steps constituting the surgery the state shown in the surgical image is. The analysis unit 12 analyzes which step is performed for each frame in a moving image or each of a plurality of continuous still images (hereinafter, also referred to as a "frame, etc.") acquired in a time series. The analysis unit 12 may perform analysis after adjusting the frames per second (fps) of the moving image. For example, by reducing the fps of the moving image, the processing load and processing time of the surgical content evaluation system 1 can be reduced.

The analysis unit 12 compares the surgical image acquired by the acquisition unit 11 with the specific region analysis model stored in the storage unit 20, and analyzes the specific region in the surgical image. The analysis unit 12 analyzes a specific region for each frame, etc. Here, in the present embodiment, the specific region is a region formed by outflow of body fluids (e.g., blood, bile, etc.) in a surgical image, and is analyzed by the analysis unit 12 as a specific region by a characteristic such as color (for example, red color which is a color of blood, yellow color which is a color of bile, white color when an organ is burnt, and black color) or edge of the region (body fluids have higher viscosity than water and thus are characterized by edges).

The analysis unit 12 compares the surgical image acquired by the acquisition unit 11 with the anatomical structure identification model stored in the storage unit 20, and analyzes the anatomical structure captured in the surgical image as an example of the body information. The analysis unit 12 analyzes an anatomical structure for each frame, etc.

In addition, the analysis unit 12 compares the surgical image acquired by the acquisition unit 11 with the instrument identification model stored in the storage unit 20, and analyzes the state of the instrument captured in the surgical image (for example, the type of the instrument and the orientation of the instrument) which is an example of the instrument information. The analysis unit 12 analyzes the state of the instrument being imaged for each frame, etc.

The time measurement unit 13 measures the inter-step period of time, which is the time from one step to the next step in a plurality of steps constituting the surgery captured in the surgical image acquired by the acquisition unit 11.

Figure 3:
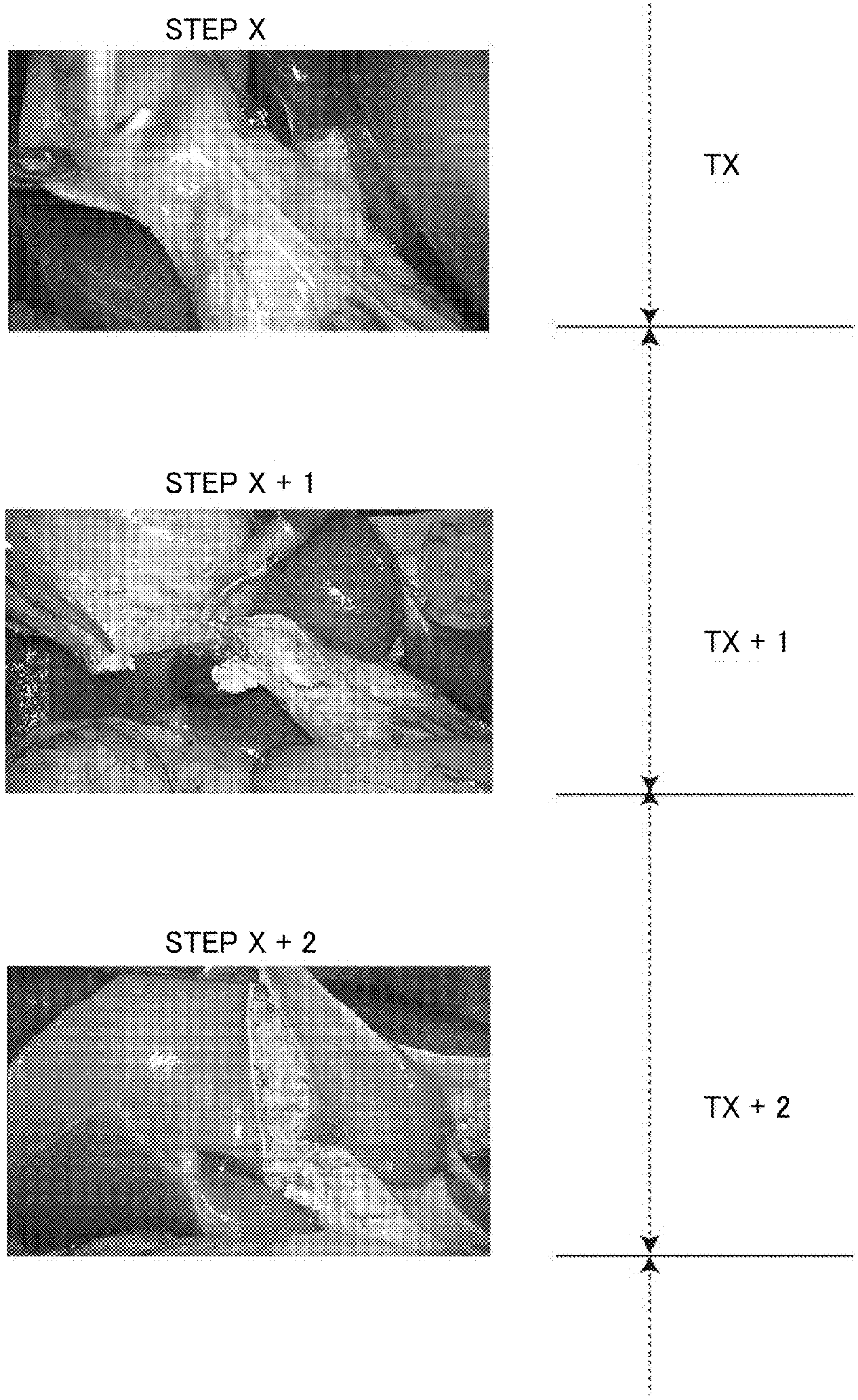
FIG. 3 is a view illustrating processing performed by a time measurement unit in the surgical content evaluation system according to the embodiment of the present invention.

FIG. 3 provides views illustrating processing performed by a time measurement unit in the surgical content evaluation system according to the embodiment of the present invention.

The example shown in FIG. 3 is a surgical image of gallbladder extraction surgery, and shows step X (expression of the gallbladder) in the gallbladder extraction surgery, step X+1 (extraction of the gallbladder tube) which is the next step to step X, and step X+2 (extraction of the gallbladder) which is the next step to step X+1, in order from the upper side in FIG. 3.

The analysis unit 12 identifies a frame or still image in which step X, step X+1, and step X+2 are captured among a plurality of continuous frames in a moving image or a plurality of continuous still images acquired in a time series by using the step recognition model.

The time measurement unit 13 measures, for example, the inter-step period of time TX+1 that is a time difference between the frame of step X, etc. identified by the analysis unit 12 and the frame of step X+1, etc.

With reference to FIG. 2 again, the evaluation unit 14 evaluates the contents of the surgery performed by the surgeon based on the body information and/or the instrument information analyzed by the analysis unit 12.

The evaluation unit 14 evaluates the surgical skill in the surgery based on the inter-step period of time measured by the time measurement unit 13 with respect to the inter-step period of time. Specifically, the storage unit 20 stores a determination table in which the time as the reference for the surgery is associated with each inter-step period of time. Further, the evaluation unit 14 compares the time as the reference for the surgical skill with the inter-step period of time of each step measured by the time measurement unit 13. For example, if the inter-step period of time is shorter than the reference time, the evaluation value for the surgical skill is set to a higher value, and if the inter-step period of time is longer than the reference time, the evaluation value for the surgery operation is set to a lower value.

Figure 4A:
FIG. 4A is a surgical image showing a state in which no bleeding is generated.
Figure 4B:
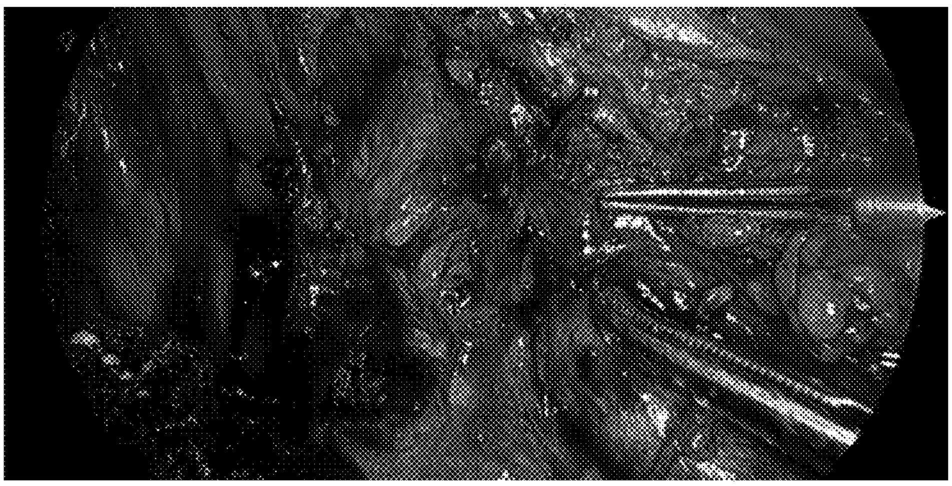
FIG. 4B is a surgical image showing a state in which bleeding has occurred.

Further, when the component of the specific color in the surgical image increases, the evaluation unit 14 evaluates that the body fluid has flowed out. FIG. 4 provides views illustrating processing of the evaluation unit in the surgical content evaluation system according to the embodiment of the present invention. FIG. 4A shows a surgical image in a state in which no bleeding is generated. FIG. 4B is a surgical image in a state in which bleeding has occurred. In the example shown in FIG. 4B, the red component, which is an example of a specific color, increases in the entire image, and the image is darker than the image shown in FIG. 4A.

The evaluation unit 14 compares the analysis result of the specific region of the surgical image by the analysis unit 12 with the specific region threshold model indicating a predetermined threshold for the size of the specific region stored in the storage unit 20, determines whether or not the size of the specific region in the surgical image has exceeded a predetermined threshold, and when the size of the specific region has exceeded a predetermined threshold, evaluates that the body fluid has flowed out or the organ has been damaged. Further, the evaluation unit 14 may evaluate the outflow of body fluid or organ damage in a stepwise manner according to the size of the specific region regardless of the size of the specific region being higher or lower than a predetermined threshold. For example, the evaluation unit 14 may use a lower evaluation value for the outflow of body fluid or organ damage as the specific region becomes larger.

In addition, the evaluation unit 14 may determine whether or not the size of the specific region has exceeded a predetermined threshold for each frame, etc., and identify the time of the frame, etc. (for example, when the surgical image is a moving image, an elapsed time from the start of the moving image or an elapsed time from the start of the surgery) at the starting point at which the size of the specific region has exceeded the predetermined threshold. By identifying such a time period, it becomes easy to confirm the surgical image before and after this time period, and to identify the operation of the instrument causing bleeding or the position of the organ where bleeding or the like occurred.

Further, the evaluation unit 14 evaluates the operation performance of the instrument in the surgery based on the information relating to the instrument included in the instrument information analyzed by the analysis unit 12.

Specifically, the evaluation unit 14 compares the analysis result of the state of the instrument for each frame, etc. by the analysis unit 12 with the anatomical structure/instrument state determination model stored in the storage unit 20, and evaluates the operation performance of the instrument in the surgery.

Here, the anatomical structure/instrument state determination model defines, for each of a plurality of steps constituting a surgery, a type serving as a reference of the instrument, an orientation serving as a reference, a route serving as a reference, a speed serving as a reference, and the like. The evaluation unit 14 compares such an anatomical structure/instrument state determination model with the analysis result of the analysis unit 12 to evaluate, for example, whether an appropriate instrument is selected, whether the instrument is appropriately used, whether ligation is appropriately performed, whether suturing is appropriately performed, or whether a blood vessel is appropriately treated.

Figure 5:
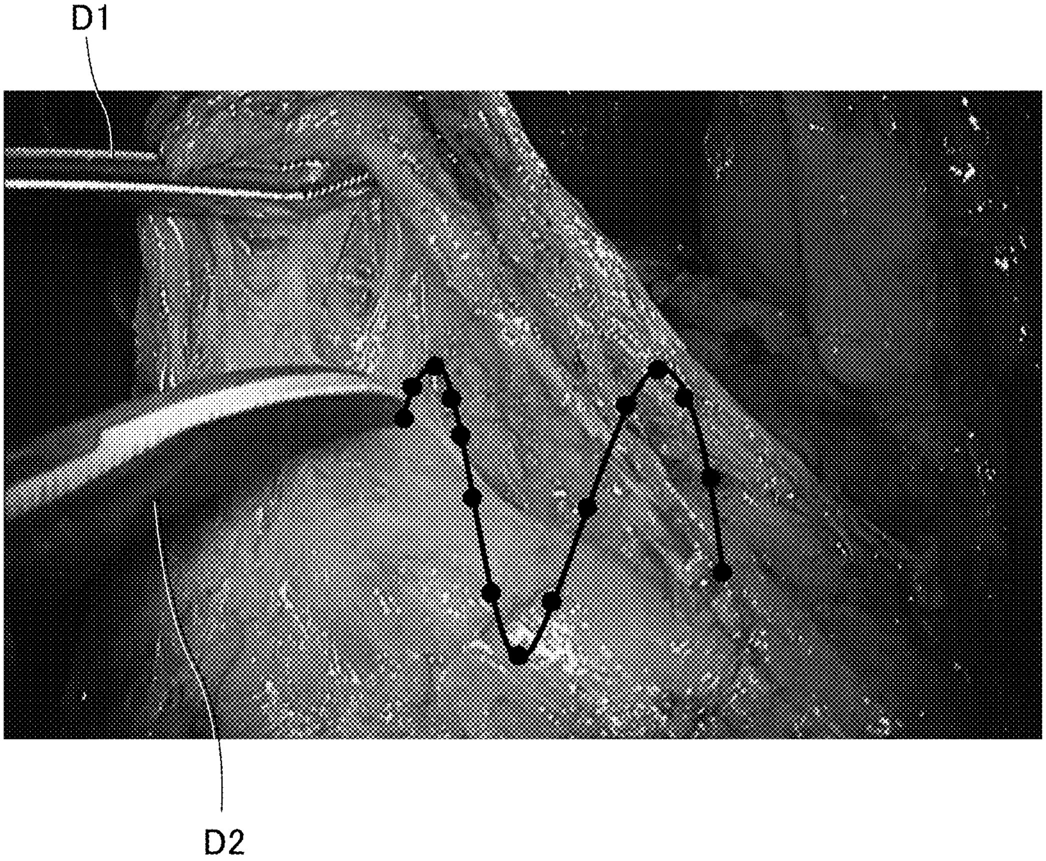
FIG. 5 is a view illustrating processing of an evaluation unit in the surgical content evaluation system according to the embodiment of the present invention.

FIG. 5 is a view illustrating processing of an evaluation unit in the surgical content evaluation system according to the embodiment of the present invention. In the example shown in FIG. 5, forceps D1 operated by the left hand (non-dominant hand) of the operator and an energy device D2 operated by the right hand of the operator are imaged.

The analysis unit 12 analyzes the state of the instrument being imaged for each frame to analyze the trajectory of the instrument (in the example shown in FIG. 5, the energy device D2) that changes in time series. In FIG. 5, points are attached to the distal end positions of the instrument in each frame, and the trajectory of the instrument is indicated by a black line connecting these points.

The evaluation unit 14 evaluates whether or not there is a straight line or a shake with respect to the trajectory analyzed by the analysis unit 12, and evaluates whether or not the instrument is appropriately used based on the total distance operated along the trajectory. As the total distance of the trajectory of such an instrument is longer than the reference value (the reference defined in the anatomical structure/instrument state determination model), the evaluation value of whether the instrument is properly used becomes lower.

The evaluation unit 14 compares the trajectory analyzed by the analysis unit 12 with the anatomical structure/instrument state determination model, thereby making it possible to evaluate, for example, whether or not there is trembling of the instrument during the operation, the constancy of the moving rate (low acceleration), whether the instrument has moved along the shortest distance from the insertion of the instrument to the position where the instrument is used, whether the instrument is stationary during use when the instrument is an energy device, whether the instrument is used in a clear and lively manner, whether blunt peeling or sharp cutting is appropriate, and whether or not the separation line is linear. Such evaluation can be used to evaluate the mental state (decrease in concentration) of the operator due to a temporal change in the nature of the trajectory during the course of surgery.

Further, the evaluation unit 14 evaluates the operation performance of the instrument with respect to the anatomical structure in the surgery based on the body information including the information relating to the anatomical structure of the body analyzed by the analysis unit 12 and the information relating to the position of the instrument with respect to the anatomical structure included in the instrument information. The information relating to the position of the instrument with respect to the anatomical structure may be included not only in the instrument information, but also in the body information and/or the instrument information.

Specifically, the evaluation unit 14 compares the analysis result of the anatomical structure and the state of the instrument for each frame, etc. by the analysis unit 12 with the anatomical structure/instrument state determination model stored in the storage unit 20 to evaluate the operation performance of the instrument with respect to the anatomical structure in the surgery.

Here, the anatomical structure/instrument state determination model defines, in terms of the anatomical structure, for each of a plurality of steps constituting the surgery, an appropriate exposed area of the connective tissue, an appropriate tension of the blood vessel or the connective tissue, an appropriate condition around the blood vessel to be ligated (for example, there is no excess organ around the ligating vessel), and the like. The evaluation unit 14 compares such an anatomical structure/instrument state determination model with the analysis result of the analysis unit 12 to evaluate whether or not the instrument is being operated at an appropriate position with respect to the anatomical structure or at an appropriate force.

In addition, the anatomical structure/instrument state determination model defines an appropriate shape and color of each organ, in addition to the above. The evaluation unit 14 compares such an anatomical structure/instrument state determination model with the analysis result of the analysis unit 12 and, when there is a difference, evaluates that an inappropriate instrument operation has been performed on an organ. For example, if the color is different from the appropriate color of the organ, it is a burn-in mark caused by an instrument (an electric scalpel or the like). Therefore, it is evaluated that an inappropriate operation of an instrument has been performed.

Figure 6A:
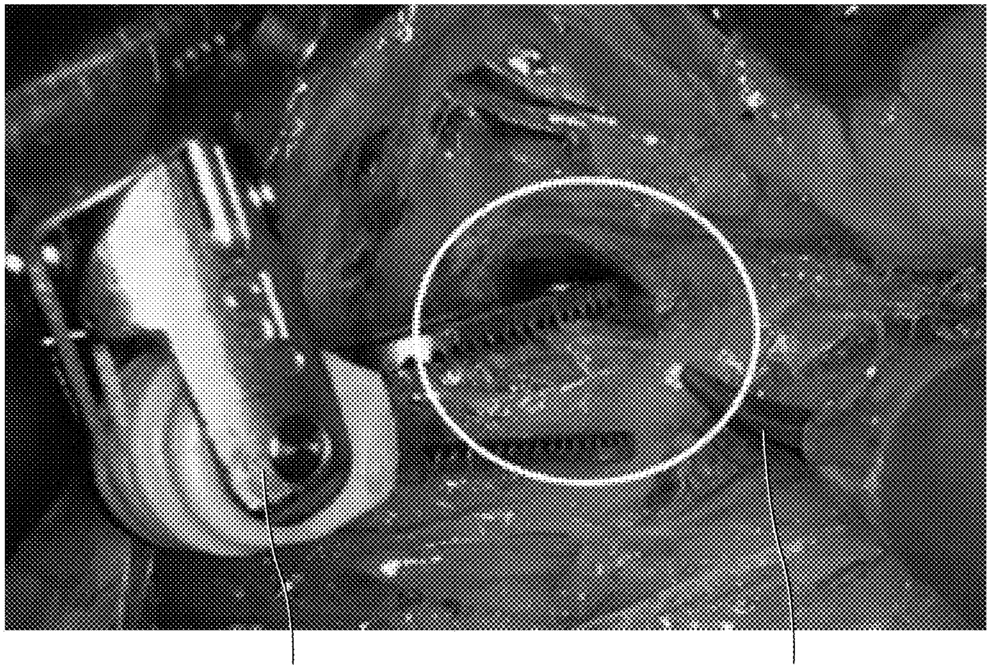
FIG. 6A shows a state in which an instrument is not appropriately operated with respect to the anatomical structure.
Figure 6B:
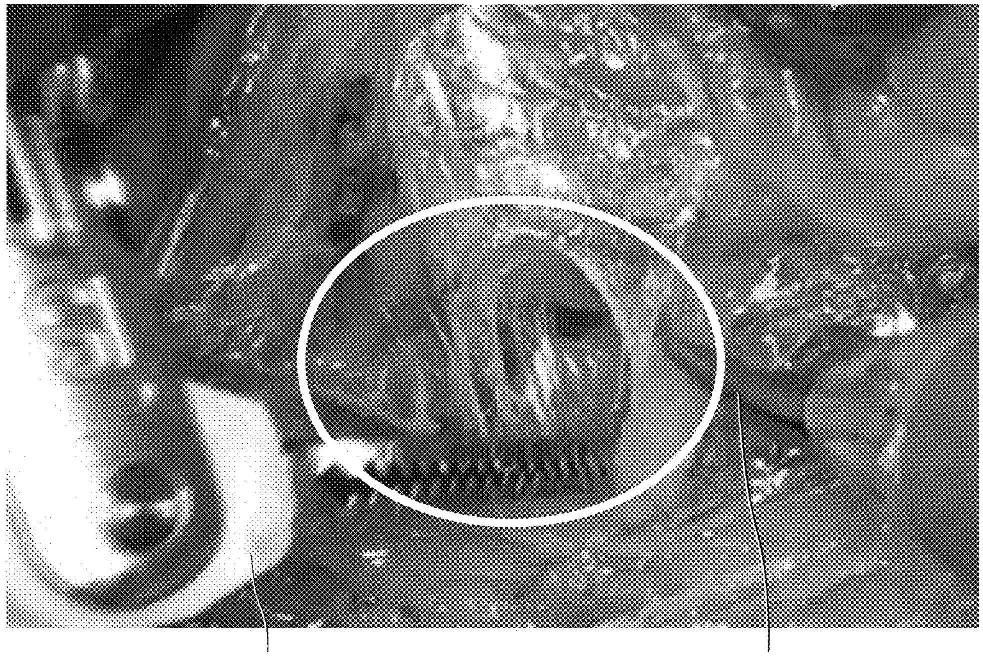
FIG. 6B shows a state in which the instrument is appropriately operated with respect to the anatomical structure.

FIG. 6 provides views illustrating processing performed by the evaluation unit in the surgical content evaluation system according to the embodiment of the present invention. FIG. 6A shows a state in which the instrument is not appropriately operated with respect to the anatomical structure. FIG. 6B shows a state in which the instrument is appropriately operated with respect to the anatomical structure.

In the example shown in FIG. 6A, an instrument (in the example shown in FIG. 6A, forceps D4) operated by the left hand (non-dominant hand) of the operator does not apply an appropriate tension to a connective tissue (portion surrounded by a white circle in the image), which is an example of an anatomical structure, a portion to be cut by the energy device D4 is close to another organ and, when the energy device D4 is brought close to the other organs, there is a risk that the other organs may be damaged.

When the state illustrated in FIG. 6A is analyzed by the analysis unit 12, the evaluation unit 14 lowers the evaluation value of the operation performance of the instrument with respect to the anatomical structure in the surgery.

In the example shown in FIG. 6B, an appropriate tension is applied to the connective tissue (a portion surrounded by a white circle in the image), which is an example of an anatomical structure by the forceps D4, and a portion to be cut by the energy device D4 is separated from other organs.

When the state illustrated in FIG. 6B is analyzed by the analysis unit 12, the evaluation unit 14 increases the evaluation value of the operation performance of the instrument with respect to the anatomical structure in the surgery. As such a state approximates the appropriate tension for the connective tissue defined in the anatomical structure/instrument state determination model closer, it is possible for the evaluation unit 14 to increase the evaluation value of the operation performance of the instrument with respect to the anatomical structure in the surgery.

Figure 7A:
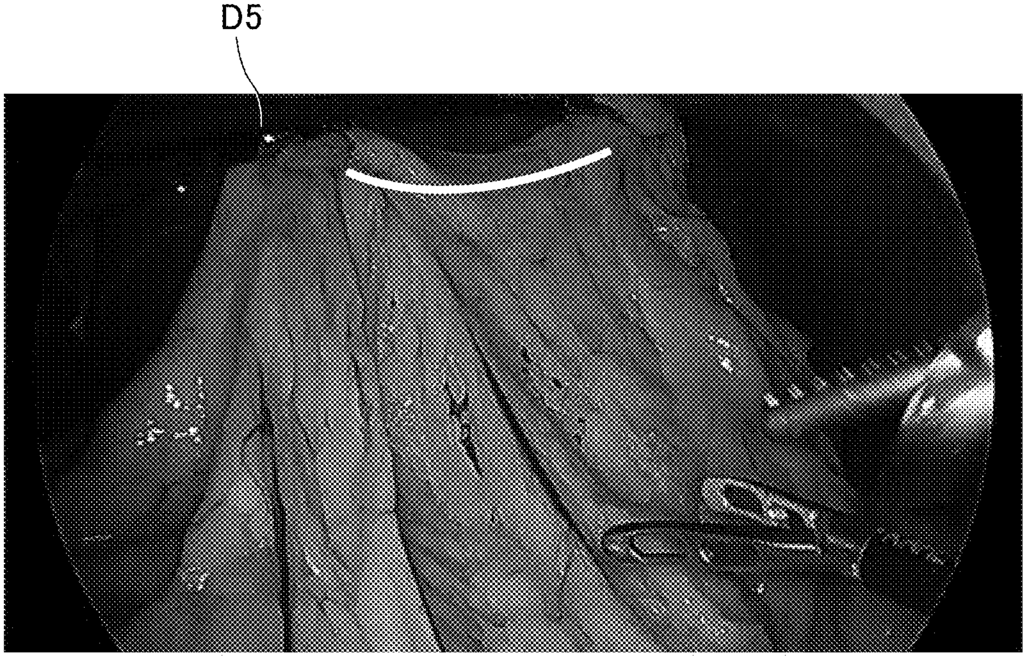
FIG. 7A shows a state in which the instrument is not appropriately operated with respect to the anatomical structure.
Figure 7B:
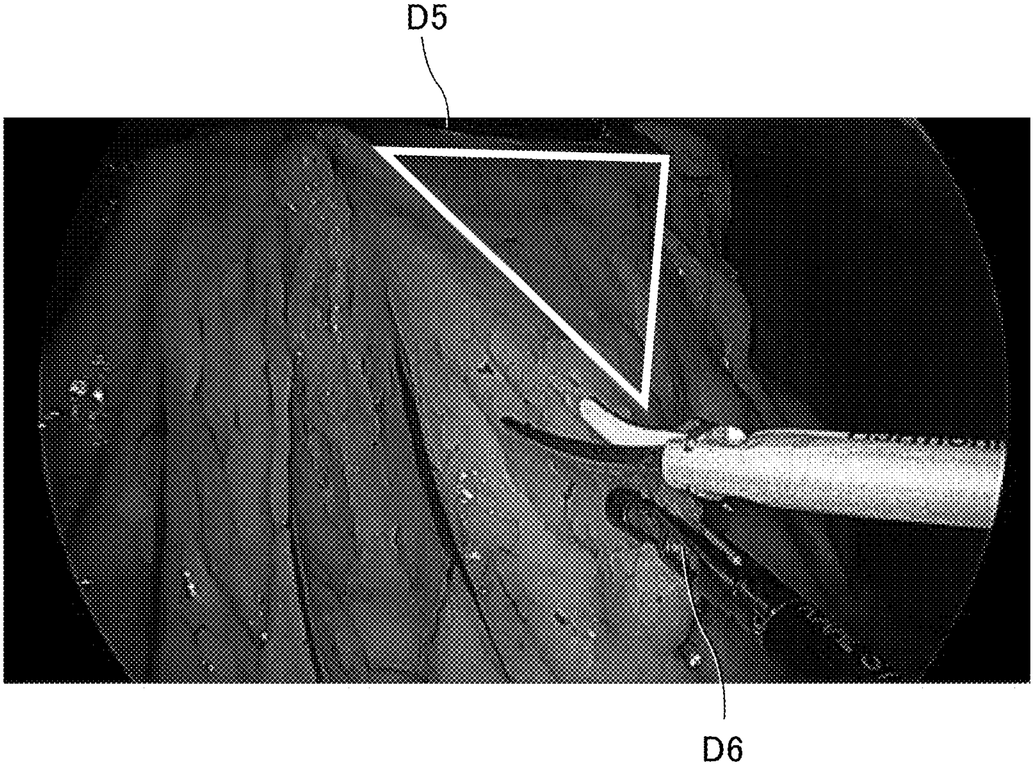
FIG. 7B shows a state in which the instrument is appropriately operated with respect to the anatomical structure.

FIG. 7 provides views illustrating processing of the evaluation unit in the surgical content evaluation system according to the embodiment of the present invention. FIG. 7A shows a state in which the instrument is not appropriately operated with respect to the anatomical structure. FIG. 7B shows a state in which the instrument is appropriately operated with respect to the anatomical structure.

In the example shown in FIG. 7A, with respect to fat, which is an example of the anatomical structure, the fat is not properly held by the instrument operated by the assistant (forceps D5 in the example shown in FIG. 7A), and slack (the white line in the upper portion of FIG. 7A) is generated. In this state, the energy device cannot cut the fat appropriately.

When the state illustrated in FIG. 7A is analyzed by the analysis unit 12, the evaluation unit 14 lowers the evaluation value in relation to the operation performance of the instrument with respect to the anatomical structure in the surgery and the cooperation with the assistant.

In the example shown in FIG. 7B, the upper portion of the fat, which is an example of the anatomical structure, is held linearly by the forceps D5 operated by the assistant, and in the lower portion, forceps D6 operated by the left hand (non-dominant hand) of the operator holds the upper portion of the fat and applies an appropriate tension to the fat, whereby the fat is treated to form an appropriate triangular shape (a white line portion in FIG. 7B) as a portion to be cut.

When the state illustrated in FIG. 7B is analyzed by the analysis unit 12, the evaluation unit 14 increases the evaluation value in relation to the operation performance of the instrument with respect to the anatomical structure in the surgery and the cooperation with the assistant. The evaluation unit 14 can further increase the evaluation value in relation to the operation performance of the instrument with respect to the anatomical structure in the surgery and the cooperation with the assistant, as the shape of the cutting position of the fat as the analysis result is approximated closer to the shape (for example, a triangular shape stretched with appropriate tension, such as a sail of a yacht) with respect to the cutting position of the fat defined in the anatomical structure/instrument state determination model.

The evaluation unit 14 associates the evaluation value determined according to the analysis result by the analysis unit 12 with each item for evaluating the contents of the surgery, and generates evaluation information that can be displayed on the medical institution terminal 2 in any form such as a table format, a graph format, or a radar format in which the evaluation values are arranged.

Further, the evaluation unit 14 may extract suggested information, which is a suggestion for prompting technology improvement according to the evaluation value, or an ideal procedure image in each evaluation item according to the evaluation value. In this case, the surgical content evaluation system 1 stores, for example, the suggested information and the procedure image corresponding to the evaluation value for each evaluation item in the storage unit 20, and the evaluation unit 14 refers to the storage unit 20 to extract the suggested information and the procedure image corresponding to the determined evaluation value. Further, the evaluation unit 14 may determine a relative evaluation value with respect to the ideal procedure image for the analysis result.

Further, the surgical content evaluation system 1 may include an image editing unit that generates a digest image of the surgical image acquired by the acquisition unit 11. The image editing unit extracts, for example, a moving image of a predetermined time period including a frame of each step in the surgery identified by the analysis unit 12 from the surgical image acquired by the acquisition unit 11 for each step, and combines these moving images to generate a digest image. Further, the image editing unit may extract a moving image of a predetermined time period including a frame in which the evaluation value by the evaluation unit 14 is evaluated to be lower than a preset reference value from the surgical image acquired by the acquisition unit 11, and may generate a digest image by combining these moving images.

With reference to FIG. 2 again, the transmission unit 15 transmits the evaluation information generated by the evaluation unit 14 to the medical institution terminal 2. Further, the transmission unit 15 may transmit the suggested information, the ideal procedure image, and the digest image extracted by the evaluation unit 14 to the medical institution terminal 2. The transmission unit 15 may transmit the digest image to the medical institution terminal 2 of the evaluator (for example, a surgeon capable of evaluating the contents of surgery in a digest image), who is a person different from the operator of the surgery. In this case, the surgical content evaluation system 1 may receive, from the medical institution terminal 2, human evaluation information indicating evaluation of the evaluator based on the transmitted digest image. The transmission unit 15 may transmit the human evaluation information together with the evaluation information generated by the evaluation unit 14 to the medical institution terminal 2.

The functional configuration of the system described above is merely an example, and one functional block (database and functional processing unit) may be divided or a plurality of functional blocks may be collectively configured as one functional block. Each function processing unit is implemented by a CPU (Central Processing Unit) built in the instrument or the terminal reading and executing a computer program (for example, the main software and an application that causes the CPU to execute the above-described various processes, or the like) stored in a storage device (storage unit) such as ROM (Read Only Memory), flash memory, a SSD (Solid State Drive), or a hard disk. Each function processing unit may include an FPGA (Field-Programmable Gate Array). That is, each function processing unit is implemented by the computer program reading and writing necessary data such as a table from a database (DB) stored in a storage device or from a storage area on memory and, in some cases, controlling related hardware (for example, a Graphics Processing Unit (GPU), an input/output device, a display device, and a communication interface device). Further, the database (DB) in the embodiment of the present invention may be a commercial database, but simply indicates a collection of tables and files, and the internal structure of the database itself is not limited.

Processing Flow

Figure 8:
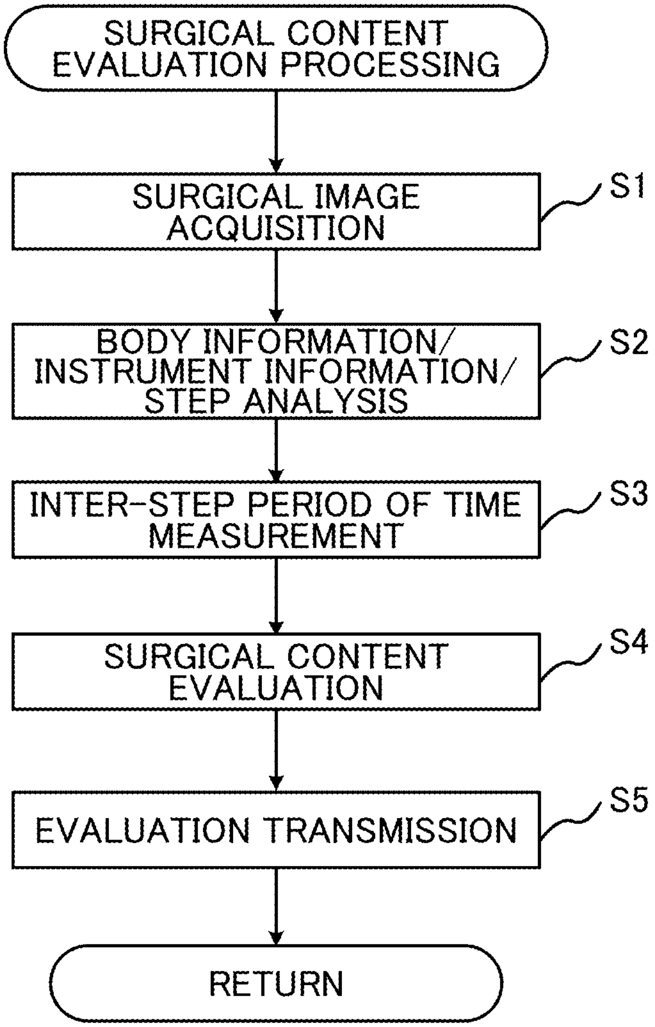
FIG. 8 is a flowchart showing surgical content evaluation processing executed by the surgical content evaluation system according to the embodiment of the present invention.

FIG. 8 is a flowchart showing surgical content evaluation processing executed by the surgical content evaluation system according to the embodiment of the present invention.

In Step S1, the acquisition unit 11 acquires, from the medical institution terminal 2 or the storage unit 20, a surgical image which is an image of the body of the patient on which the surgery is performed by the surgeon.

In Step S2, the analysis unit 12 analyzes body information indicating the state of the body and/or instrument information indicating the state of the instrument operated by the surgeon in the surgical image acquired by the acquisition unit 11 in Step S1. In this step, the analysis unit 12 analyzes a color component of a specific color (e.g., red color as blood color or yellow color as bile color) in the surgical image acquired by the acquisition unit 11 in Step S1.

In Step S3, the time measurement unit 13 measures the inter-step period of time, which is the period of time from one step to the next step in a plurality of steps constituting the surgery captured in the surgical image acquired by the acquisition unit 11 in Step S1.

In Step S4, the evaluation unit 14 evaluates the surgical skill in the surgery based on the inter-step period of time measured by the time measurement unit 13 with respect to the inter-step period of time. Further, in this step, the evaluation unit 14 determines whether or not the component of the specific color has increased in the surgical image based on the analysis result of the color component of the specific color of the surgical image by the analysis unit 12 in Step S2, and when it is determined that the component of the specific color has increased, the evaluation unit 14 evaluates that the body fluid has flowed out. In this step, the evaluation unit 14 evaluates the operation performance of the instrument in the surgery based on the information relating to the instrument included in the instrument information analyzed by the analysis unit 12 in Step S2. In this step, the evaluation unit 14 evaluates the operation performance of the instrument with respect to the anatomical structure in the surgery based on the body information including the information relating to the anatomical structure of the body and the information relating to the position of the instrument with respect to the anatomical structure included in the instrument information, which are analyzed by the analysis unit 12 in Step S2. Then, in this step, the evaluation unit 14 generates evaluation information capable of displaying the evaluation on the medical institution terminal 2.

In Step S5, the transmission unit 15 transmits the evaluation information generated by the evaluation unit 14 in Step S4 to the medical institution terminal 2.

According to the surgical contents evaluation system 1, since the contents of the surgery performed by the surgeon are evaluated based on the body information indicating the state of the body and/or the instrument information indicating the state of the instrument operated by the surgeon in the surgical image obtained by imaging the body of the patient on which the surgery is performed by the surgeon, it is possible to objectively evaluate the contents of the actual surgery. Accordingly, it is possible to provide the surgical content evaluation system capable of objectively evaluating the content of an actual surgery.

Further, according to the surgical content evaluation system 1, when the component of the specific color in the surgical image increases, it is possible to objectively evaluate the organ damage, which is an important evaluation target, by evaluating that the body fluid has flowed out.

Further, according to the surgical content evaluation system 1, by evaluating the operation performance of the instrument in the surgery based on the information relating to the instrument included in the instrument information, it is possible to objectively evaluate the operation performance of the instrument not only based on the result of the feeling of the operator, the absence of organ damage, or the like.

Further, according to the surgical content evaluation system 1, by evaluating the operation performance of the instrument with respect to the anatomical structure in the surgery based on the information relating to the position of the instrument with respect to the anatomical structure, it is possible to objectively evaluate the operation performance of the instrument with respect to the anatomical structure not only based on a result of the feeling of the operator, the absence of the damage to the organ, or the like, but also objectively evaluate a possibility of leading to a mistake such as the damage to the organ.

Further, according to the surgical content evaluation system 1, since the surgical skill in the surgery is evaluated based on the inter-step period of time which is the time from a certain step to the next step, it is possible to objectively evaluate not only the time of the entire surgery, but also the surgical skill of the operator for each step.

Application Example

Next, an application example of the embodiment of the present invention will be described. In the following description, the same components as in the present embodiment are denoted by the same reference numerals, and the description thereof will be omitted or simplified. In the surgical content evaluation system 1 according to the application example, in addition to the configuration of the present embodiment, mainly the analysis unit 12 (see FIG. 2) calculates the recognition degree indicating the degree of recognition of the body information, and the evaluation unit 14 (see FIG. 2) evaluates the content of the surgery performed by the surgeon according to the recognition degree.

In the application example, the "recognition degree" refers to the degree of the number of pixels and the area in which the confidence degree indicates the degree of confidence of the analysis result by the analysis unit 12 with respect to the surgical image is equal to or greater than a certain threshold, the total amount of the confidence degree, or the speed and acceleration of the increase or decrease in them, or the continuity (non-interruption or the like) of a structure such as an organ.

Figure 9:
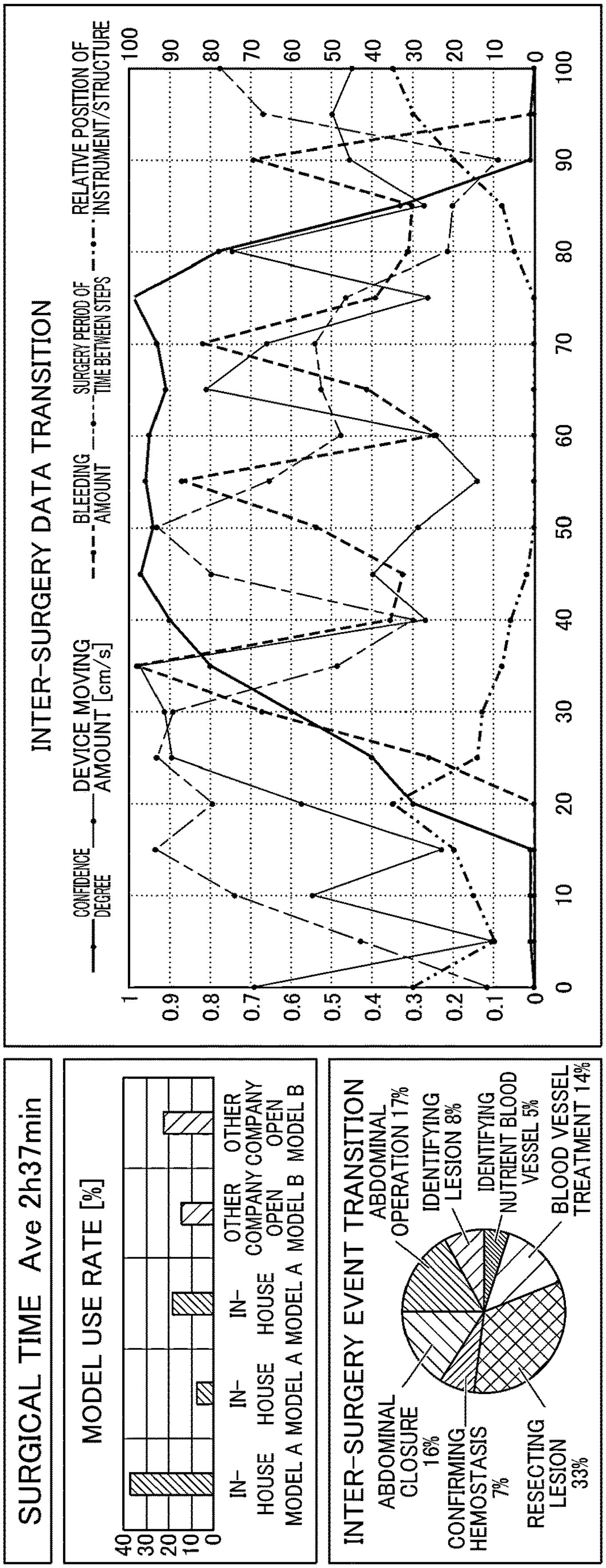
FIG. 9 provides diagrams showing an example of evaluation information generated in the surgical content evaluation system according to the application example of the embodiment of the present invention.

FIG. 9 provides diagrams showing an example of evaluation information generated in the surgical content evaluation system according to the application example of the embodiment of the present invention. The example shown in FIG. 9 is an example of the evaluation information generated by the evaluation unit 14 and displayable on the medical institution terminal 2, and the evaluation value determined according to the analysis result by the analysis unit 12 is shown in a graph format.

For example, in the example shown in FIG. 9, the graph on the right side in the figure represents data transition during surgery, and the horizontal axis represents elapsed time during surgery (in the example shown in FIG. 9, the surgery start time is 0, and the surgery end time is 100), and the vertical axis represents the degree of each item. This graph includes, as items, confidence degree, device movement amount, bleeding amount, surgical time between steps, and relative position of instrument/structure. These items are each shown in a graph showing its transition, and these graphs are superimposed on the same time axis. With such evaluation information, it is possible to evaluate the contents of the surgery based on the relationship between the probability (confidence degree) indicating the degree of confidence of the analysis result calculated when the analysis unit 12 (AI) performs the analysis and the analysis result by the analysis unit 12 (device movement amount, bleeding amount, surgical time between steps, relative position of instrument/structure, etc.).

Further, as shown on the left side of FIG. 9, the evaluation information may include information indicating an event transition (the elapsed time of each event) during the operation in a circular graph, information indicating the usage rate of the AI model used by the analysis unit 12 or the evaluation unit 14, and information indicating the operation time.

(Evaluation using Recognition Degree of Anatomical Structure)

The analysis unit 12 calculates a recognition degree indicating a degree of recognition of body information (e.g., anatomical structure) in the surgical image. More specifically, the analysis unit 12 calculates a confidence degree indicating the degree of confidence of the analysis result of the body information, and calculates the recognition degree based on the confidence degree. The evaluation unit 14 evaluates the contents of the surgery performed by the surgeon in accordance with the recognition degree.

Figure 10:
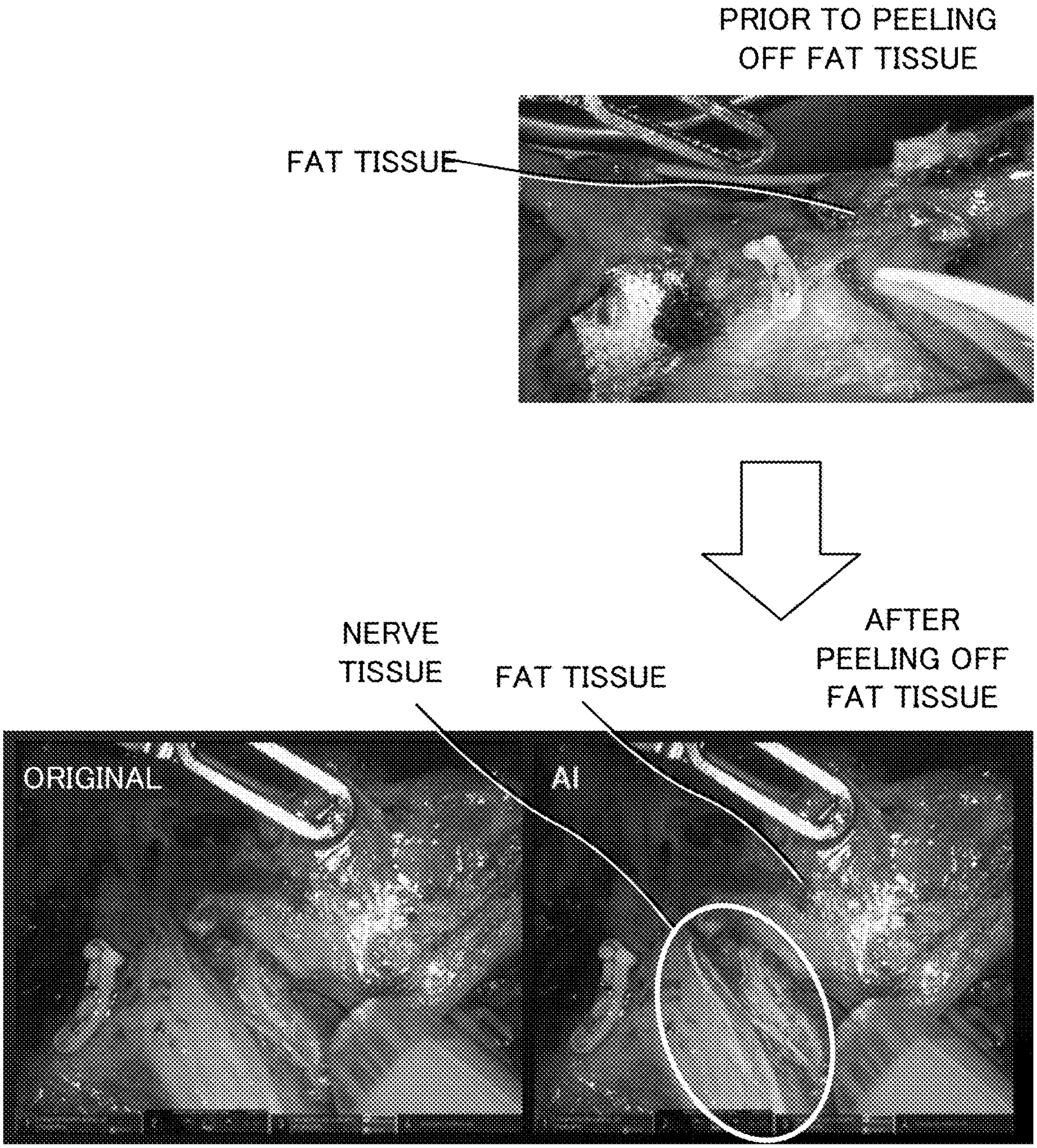
FIG. 10 provides views illustrating processing of an evaluation unit in the surgical content evaluation system according to an application example of the embodiment of the present invention.

FIG. 10 provides views illustrating processing of the evaluation unit in the surgical content evaluation system according to the application example of the embodiment of the present invention. FIG. 10 shows surgical images of the step of peeling off a fatty tissue and exposing nerves. The nerve tissue is not exposed in the surgical image (upper image) before peeling off the fatty tissue. Then, it can be confirmed that the surgery progresses and the nerve tissue is exposed in the surgical image (lower image) after the peeling off the fatty tissue, the nerve tissue is not severed, and the nerve tissue is continuous.

In the surgical image (lower image) after peeling off the fatty tissue shown in FIG. 10, the left image shows an original image captured by a camera, and the right image shows the original image in which the nerve tissue is identified and colored by analysis of the analysis unit 12. The analysis unit 12 analyzes the portion of the surgical image in which the nerve tissue is displayed, and colors the portion of the analysis result in which the confidence degree has exceeded a predetermined threshold.

For example, in a case where the fatty tissue is insufficiently peeled off, or in a case where there is an ablation trace in which the nerve tissue is burned by an electric scalpel or the like, the exposed area of the nerve tissue (the area of the portion where the confidence degree has exceeded a predetermined threshold) becomes smaller than the example shown in the surgical image after the fatty tissue is peeled off in FIG. 10. The contents of such surgery are considered to be low in evaluation. In such a case, the recognition degree of the nerve tissue, which is an example of the body information calculated by the analysis unit 12, decreases as compared with the case where the nerve tissue is sufficiently exposed and the nerve tissue is not interrupted. When the recognition degree decreases, the evaluation unit 14 evaluates the contents of the surgery performed by the surgeon to be low.

The analysis unit 12 may calculate the exposure area of the target organ (the sum of the number of pixels whose confidence degree has exceeded the threshold), which is an example of the body information, thereby calculating the recognition degree, calculate the total amount of the confidence degree of the target organ, calculate the recognition degree based on the continuity of the target organ, or may calculate the recognition degree by combining these.

One criterion for a good operation is that vital organs to be preserved, such as blood vessels, ureters, seminal tubes, and pancreas, in addition to nerves, should be cleanly exposed (in a state in which the organs are peeled off from surrounding tissues and there is no severing). Therefore, when the rate of increase of the exposed area of the preserved organ is high, it is shown that the preserved organ is exposed smoothly, and thus, it is good in evaluation. Based on such evaluation criteria, the evaluation unit 14 may evaluate the contents of the surgery performed by the surgeon in accordance with the temporal change of the recognition degree. Specifically, the evaluation unit 14 may evaluate the contents of the surgery in accordance with the speed or acceleration of the increase or decrease of the recognition degree. For example, the evaluation unit 14 may evaluate that the surgery progresses quickly when the rate of the increase/decrease of the recognition degree is fast, or may evaluate that the surgery progresses stably when the acceleration of the increase/decrease of the recognition degree is constant.

The evaluation unit 14 may generate a learning model obtained by AI learning a good evaluation example (an example of good surgery in evaluation) and a poor evaluation example (an example of poor surgery in evaluation) in which the analysis result of the analysis unit 12 is reflected, and may perform evaluation using the learning model. Specifically, the good surgery is a surgery not causing a complication of surgery, a surgery that is performed by a skilled physician, a surgery that a skilled physician determines that the surgery is a good surgery, or the like. The poor surgery is a surgery causing a complication of surgery, a surgery that is performed by an unfamiliar doctor, a surgery that a skilled physician determines that the surgery is a poor surgery, or the like. The evaluation unit 14 assigns these as correct data to learn the evaluation using the AI and determines good and poor in evaluation.

Figure 11:
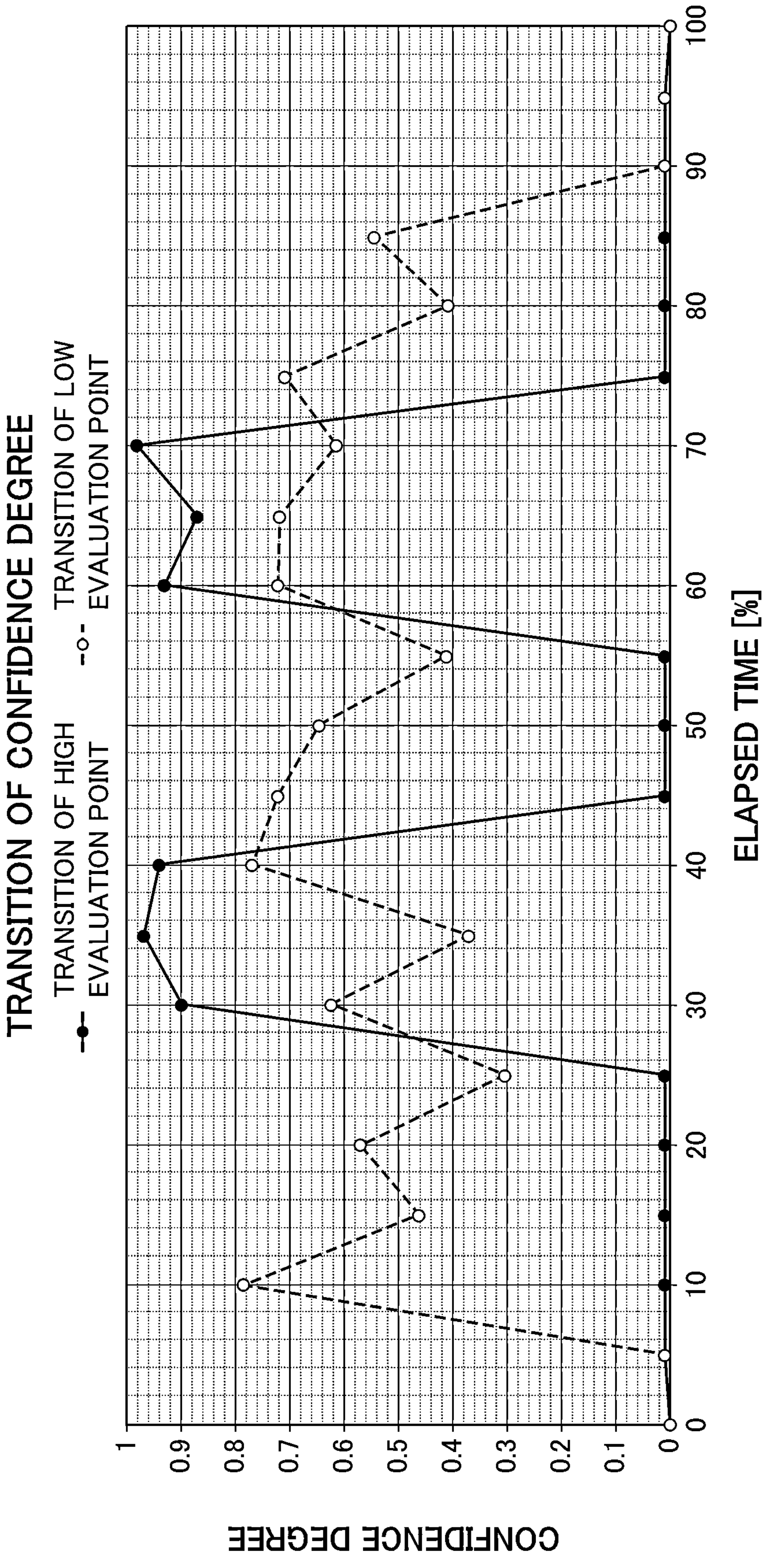
FIG. 11 is a diagram showing an example of evaluation information generated in the surgical content evaluation system according to the application example of the embodiment of the present invention.

FIG. 11 is a diagram showing an example of evaluation information generated in the surgical content evaluation system according to the application example of the embodiment of the present invention. FIG. 11 shows an example of the evaluation information generated by the evaluation unit 14 and displayable on the medical institution terminal 2, and the evaluation values determined according to the analysis result by the analysis unit 12 are shown in a graph format. The example shown in FIG. 11 shows the transition of the confidence degree of the resected organ in the surgery for resecting the organ. In the example, an example having high evaluation points by the evaluation unit 14 and an example having low evaluation points by the evaluation unit 14 are shown in a superimposed manner.

As shown in FIG. 11, the evaluation unit 14 determines a higher evaluation point as the highest value of the confidence degree with respect to the analysis result of the resected organ is higher (well exposed, less camera blurring, and less bleeding) and as the period of time of the confidence degree equal to or less than 0.1 is longer (since appropriate resection is performed, there is no or very few portions analyzed with the resected organ).

The evaluation index of the evaluation in the evaluation unit 14 is not limited to the confidence degree, and may be a pixel amount or an increase/decrease rate (processing time is fast) of a pixel amount having a confidence degree equal to or greater than a certain value, or may be a constant increase/decrease rate (no blur in the procedure). As described above, the evaluation unit 14 may evaluate the contents of the surgery performed by a surgeon in accordance with not only the recognition degree based on the confidence degree, but also the recognition degree based on other degrees.

Figure 12:
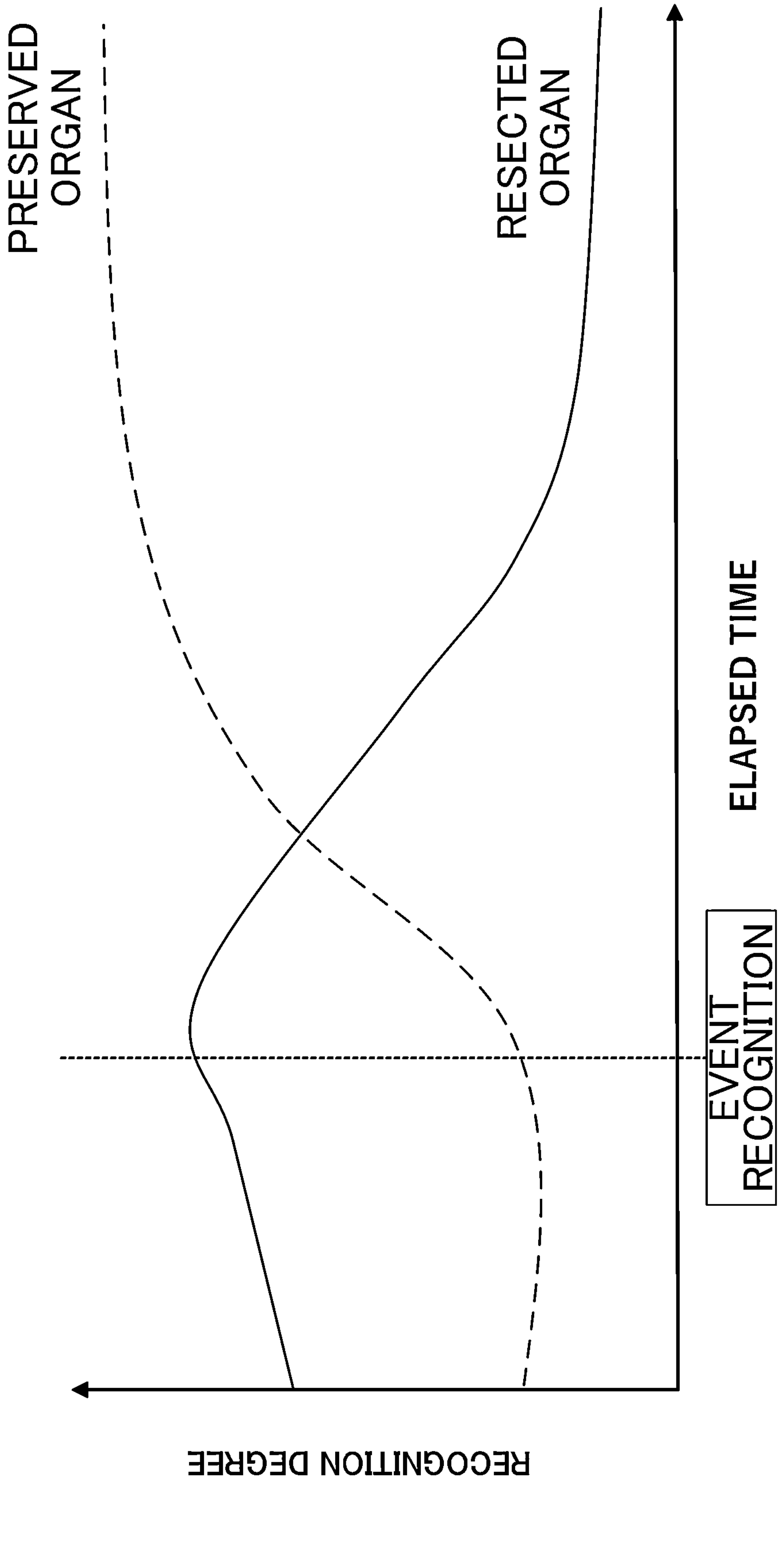
FIG. 12 is a diagram showing an example of evaluation criteria in an evaluation unit of the surgical content evaluation system according to the application example of the embodiment of the present invention.

FIG. 12 is a diagram showing an example of evaluation criteria in the evaluation unit of the surgical content evaluation system according to the application example of the embodiment of the present invention. Here, in surgery, a resected organ or an organ to be resected and a preserved organ or an organ to be preserved are mixed. FIG. 12 shows temporal changes in the recognition degrees of the resected organ and the preserved organ in such a case.

The evaluation unit 14 recognizes a surgical scene (recognition of an event of resecting an organ to be resected from a preserved organ) based on the analysis result of the anatomical structure and the state of the instrument (such as the type of instrument being used) by the analysis unit 12. The evaluation unit 14 evaluates the contents of the surgery performed by the surgeon based on the change in the recognition degree of the resected organ (e.g., connective tissue) and the change in the recognition degree of the preserved organ (nerves) after the recognition of the event. For example, when the recognition degree of the resected organ decreases and the recognition degree of the preserved organ increases after the recognition of the event, the evaluation unit 14 determines that the evaluation point is higher.

Evaluation of Recognition of Instrument

Figure 13:
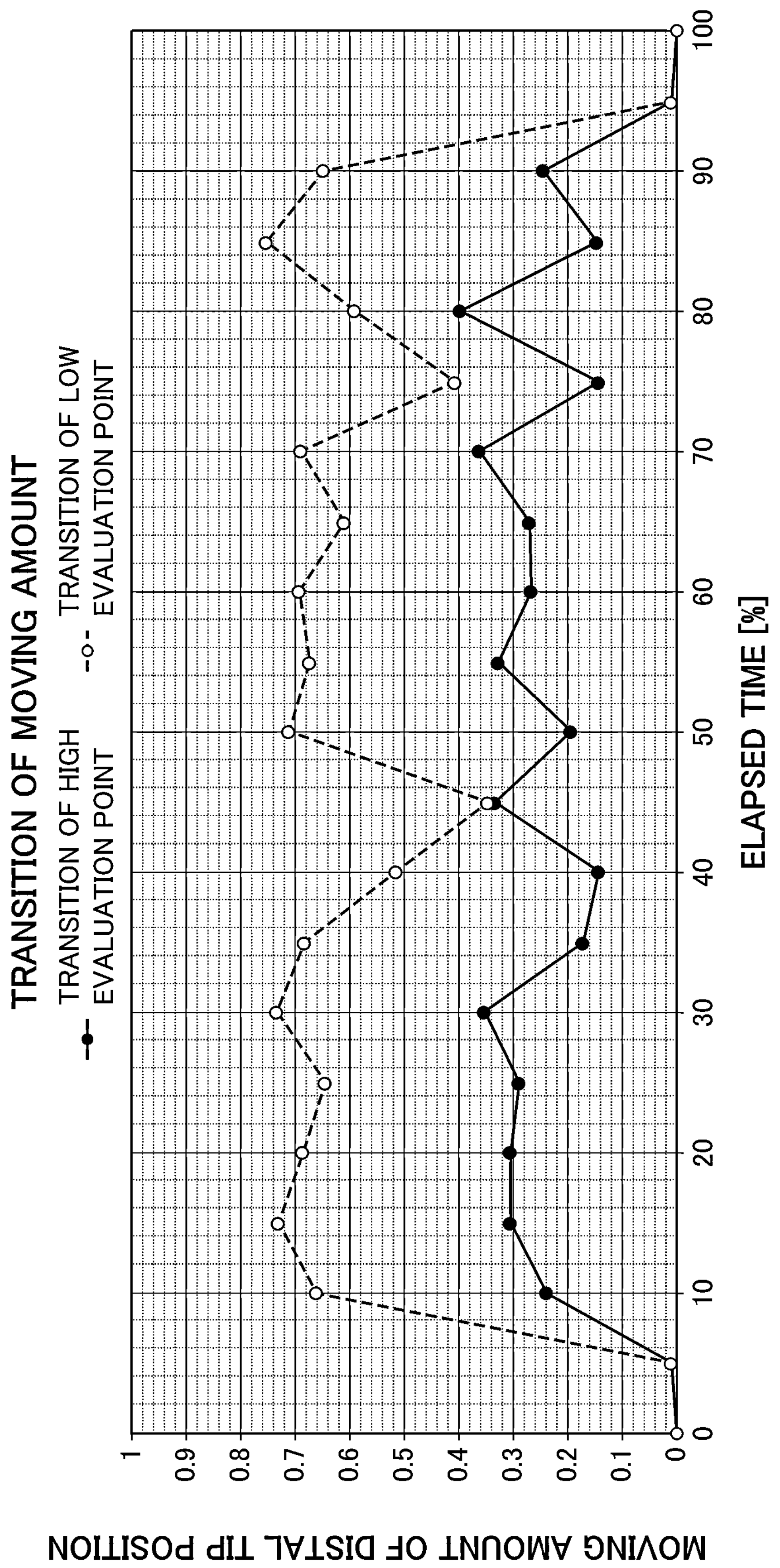
FIG. 13 is a diagram showing an example of evaluation information generated in the surgical content evaluation system according to the application example of the embodiment of the present invention.

FIG. 13 is a diagram showing an example of evaluation information generated in the surgical content evaluation system according to the application example of the embodiment of the present invention. FIG. 13 shows an example of the evaluation information generated by the evaluation unit 14 and displayable on the medical institution terminal 2, and the movement amount calculated according to the analysis result by the analysis unit 12 is shown in a graph format. The example shown in FIG. 13 shows the transition of the movement amount in the trajectory of the distal end position of the instrument being operated by the surgeon. In the example, an example having a higher evaluation point by the evaluation unit 14 and an example having a lower evaluation point by the evaluation unit 14 are shown in a superimposed manner.

As shown in FIG. 13, as the movement amount of the instrument is smaller, it can be estimated that the surgery has been performed efficiently. Therefore, the evaluation unit 14 determines a higher evaluation point.

Similarly to the present embodiment, the analysis unit 12 analyzes the trajectory (see FIG. 5) of the distal end position of the instrument. Further, as in the present embodiment, the evaluation unit 14 evaluates whether or not there is a straight line or blurring with respect to the trajectory analyzed by the analysis unit 12, and evaluates whether or not the instrument has been appropriately used based on the total distance operated along the trajectory. The total distance and blurring in the trajectory of the distal end position of the instrument increase in proportion to wasteful movement of the instrument, resulting in a technical evaluation for the operator. When the instrument is gripping forceps, the evaluation unit 14 may evaluate whether or not the instrument has been appropriately used based on the frequency of opening and closing of the distal end portion. Further, the evaluation unit 14 may evaluate the operation performance of the instrument in the surgery based on the speed calculated from the distance between the distal end positions of the instruments between the adjacent frames and the acceleration measured by the gyrocenter (forceps side) or the like. In addition, the analysis unit 12 analyzes the positional relationship between a point of action (for example, a tip of a forceps or a cutting tool) which is a portion of the instrument operated by the surgeon that is in contact with the anatomical structure, and a portion of the anatomical structure that is in contact with the instrument (for example, a portion gripped by the forceps or a portion cut by the cutting tool). Specifically, it is possible to perform evaluation by making an image of a portion holding a tissue including an anatomical structure and an instrument, making correct data indicating whether or not the tissue can be appropriately held, and creating an AI learning model (anatomical structure/instrument state determination model). For example, a good evaluation refers to a good surgical operation in which the confidence degree of the gripped state is high. By performing AI learning on a state in which some kind of processing is performed, the present invention is applicable to a cutting tool or the like.

Evaluation using Positional Information of Instrument and Structure

As in the present embodiment, the evaluation unit 14 evaluates the operation performance of the instrument with respect to the anatomical structure in the surgery based on the body information including the information relating to the anatomical structure of the body analyzed by the analysis unit 12 and the information relating to the position of the instrument with respect to the anatomical structure included in the instrument information. Further, the evaluation unit 14 may evaluate the contents of the surgery using positional information of the anatomical structure of the body analyzed by the analysis unit 12 and the instrument such as forceps, etc. (for example, a positional relationship between a point of action, which is a portion of the instrument operated by the surgeon in contact with the anatomical structure, and a portion of the anatomical structure in contact with the instrument). Specifically, the evaluation unit 14 may evaluate whether or not the organ is gripped at an appropriate position by the forceps based on the position information of the anatomical structure and the tip of the forceps.

In this case, the evaluation unit 14 can evaluate the contents of the surgery based on the absolute position of the anatomical structure and the instrument in three dimensions, the absolute position of the anatomical structure and the instrument in two dimensions, the relative position of the anatomical structure and the instrument in three dimensions, or the relative position of the anatomical structure and the instrument in two dimensions.

Figure 14:
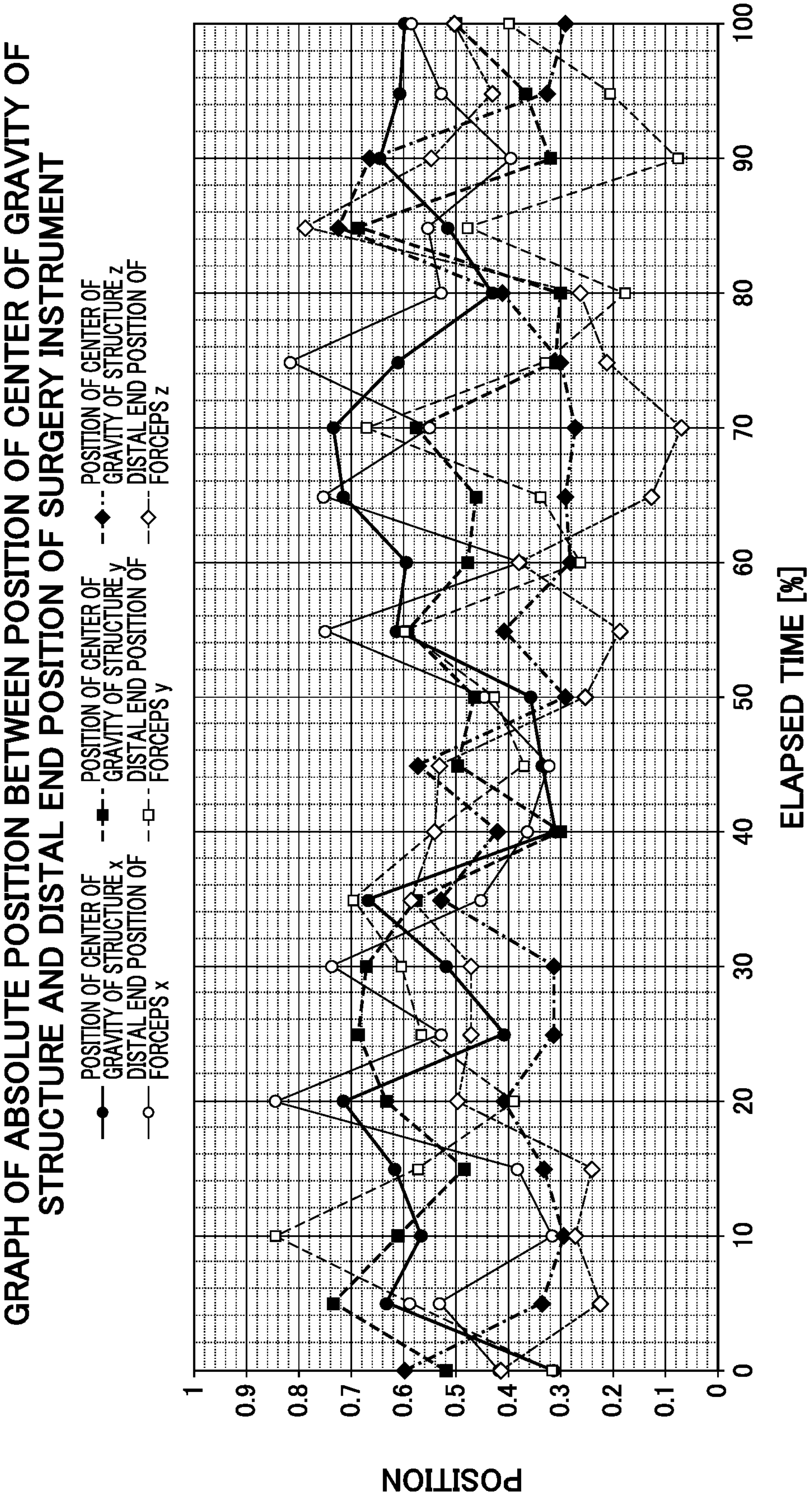
FIG. 14 is a diagram showing an example of evaluation information generated in the surgical content evaluation system according to the application example of the embodiment of the present invention.

FIG. 14 is a diagram showing an example of evaluation information generated in the surgical content evaluation system according to the application example of the embodiment of the present invention. FIG. 14 shows an example of evaluation information generated by the evaluation unit 14 and displayable on the medical institution terminal 2, and the anatomical structure and the position of the distal end of a surgical instrument calculated according to the analysis result by the analysis unit 12 are shown in a graph format. The example shown in FIG. 14 shows the transition between the three-dimensional absolute position of the center of gravity of the structure (anatomical structure) and the three-dimensional absolute position of the distal end position of the surgical instrument. Specifically, the transitions of the positions of the center of gravity of the structure in the x, y, and z directions and the positions of the distal end position of the surgical instrument in the x, y, and z directions are shown. The center of gravity of the structure refers to the position of the center of gravity (1/2 point, 1/3 point, or the like) of the area of a portion analyzed as the target structure (e.g., pancreas) by the analysis unit 12. Instead of the center of gravity of the structure, the position of the outline of the portion (upper edge, lower edge, left edge, right edge) may be used.

Figure 15:
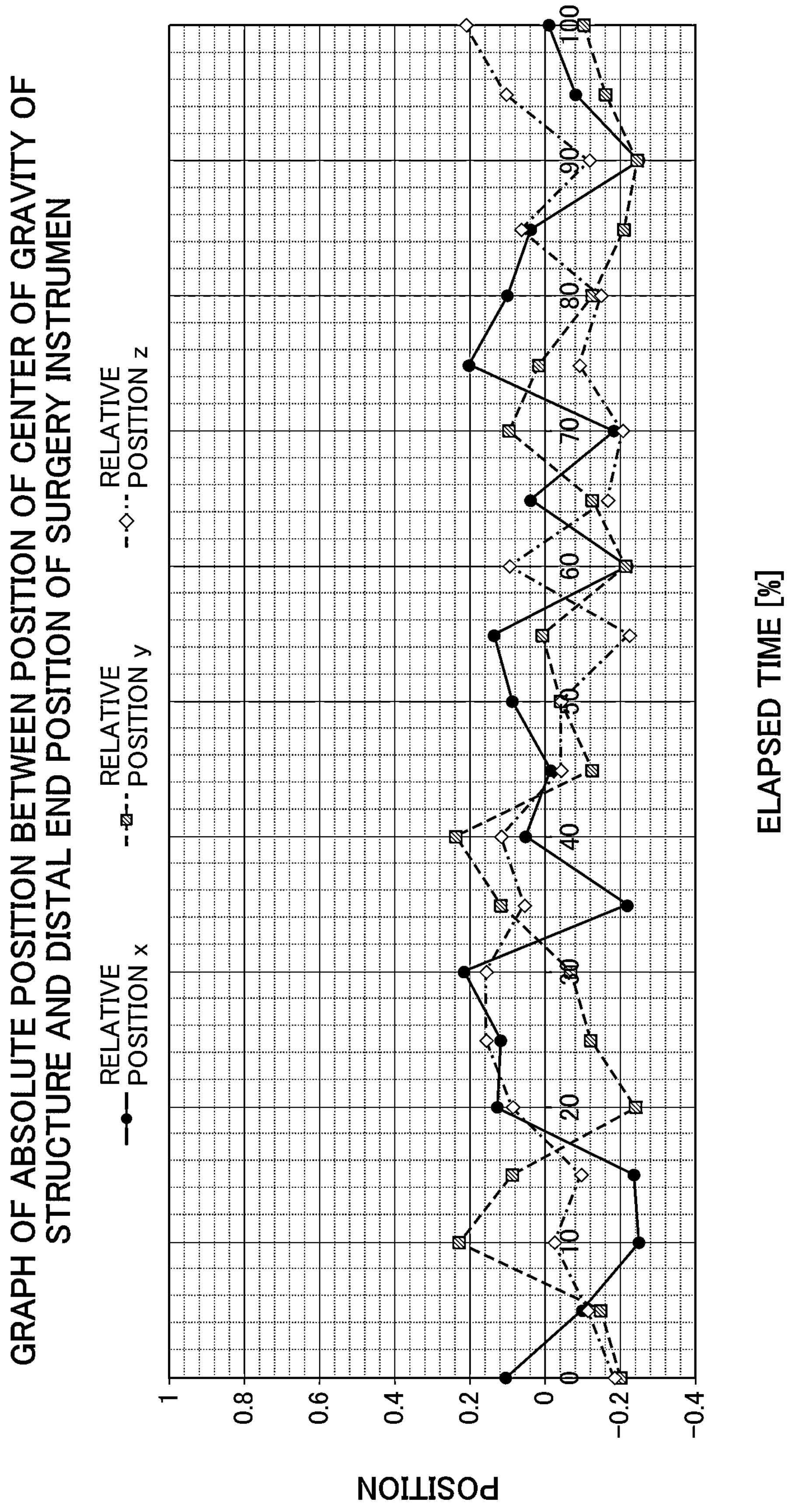
FIG. 15 is a diagram showing an example of evaluation information generated in the surgical content evaluation system according to the application example of the embodiment of the present invention.

FIG. 15 is a diagram showing an example of evaluation information generated in the surgical content evaluation system according to the application example of the embodiment of the present invention. FIG. 15 is an example of evaluation information generated by the evaluation unit 14 and displayable on the medical institution terminal 2, and the relative positions of the anatomical structure and the distal end of the surgical instrument calculated according to the analysis result by the analysis unit 12 are shown in a graph format. The example shown in FIG. 15 shows the transition of the relative positions between the center of gravity of the structure (anatomical structure) and the distal end of the surgical instrument. Specifically, the transition of the relative positions between the center of gravity of the structure and the tip of the surgical instrument in the x, y, and z directions are shown.

The evaluation unit 14 evaluates the contents of the surgery based on the transition in the positional relationship between the anatomical structure and the instrument according to the type of the anatomical structure and the contents of the surgery. For example, when the anatomical structure is an organ to be preserved, the evaluation unit 14 evaluates the contents of the surgery higher when the instrument (cutting tool) used for the cutting purpose is farther from the organ to be preserved. When the anatomical structure is an organ to be resected, the evaluation unit 14 evaluates the contents of the surgery higher when the cutting tool and the organ to be resected are closer to each other. In this case, the evaluation unit 14 may evaluate the contents of the surgery higher when the relative position of the cutting tool and the organ to be resected becomes close to each other at a higher speed or when the acceleration is constant.

Alternatively, the evaluation information shown in FIG. 14 and FIG. 15 may be cumulatively recorded in the storage unit 20, and the evaluation information may be divided into appropriate surgery (for example, surgery in which no adverse event occurred, surgery performed by an experienced surgeon, and the like) and inexperienced surgery (surgery in which adverse events occurred, surgery performed by an inexperienced surgeon, etc.), boundary points between the skillful surgery and the unfamiliar surgery may be calculated by averaging each of them, and a learning model for evaluating the contents of the surgery may be generated based on the transition of the positional relationship between the anatomical structure and the instrument through AI learning. Thus, the evaluation unit 14 can evaluate the contents of the surgery based on the transition of the positional relationship between the anatomical structure and the instrument using such boundary points and the learning model.

Figure 16A:
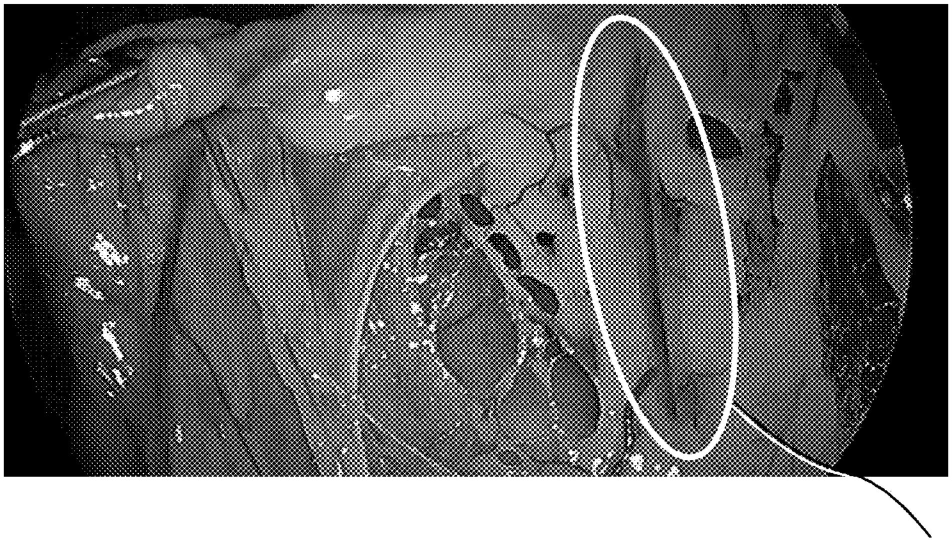
FIG. 16A is a surgical image of a lean patient.
Figure 16B:
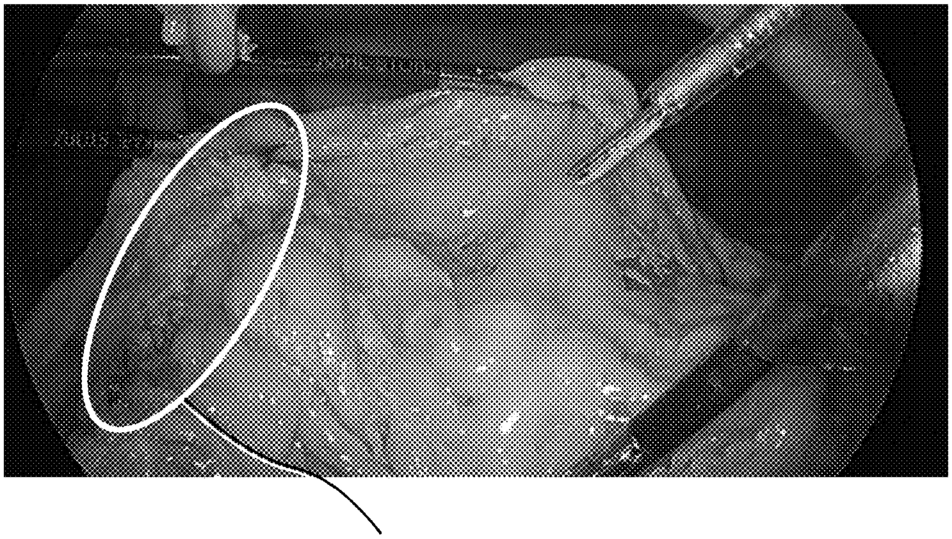
FIG. 16B is a surgical image of an obese patient.

Evaluation of Difficulty Level of Surgery depending on Recognition Degree of Anatomical Structure The evaluation unit 14 evaluates the difficulty level of the surgery according to the information relating to the anatomical structure of the body included in the body information. FIG. 16 provides views illustrating processing of an evaluation unit in the surgical content evaluation system according to the embodiment of the present invention. FIG. 16A is a surgical image of a lean patient. FIG. 16B is a surgical image of an obese patient.

As shown in FIG. 16A, in a case where the patient is of a lean type, since the amount of fat is small, the blood vessels can be seen well, resulting in a low difficulty level surgery. On the other hand, when the patient is of obesity type, fat adheres to the target organ, and blood vessels are not seen, resulting in a high difficulty level surgery. The evaluation unit 14 evaluates the difficulty level of surgery by evaluating the amount of area of adhesion, etc., composed of fat, blood vessels, and connective tissue early in the surgery. Further, the evaluation unit 14 may correct the final evaluation value of the contents of the surgery based on the evaluation early in the surgery. In addition, when the evaluation unit 14 evaluates a high difficulty level of surgery early in the surgery, the evaluation unit 14 may transmit warning information indicating a warning or suggestion such as a high bleeding risk to the terminal of the medical institution.

Evaluation of Bleeding Frequency and Bleeding Area

Figure 17:
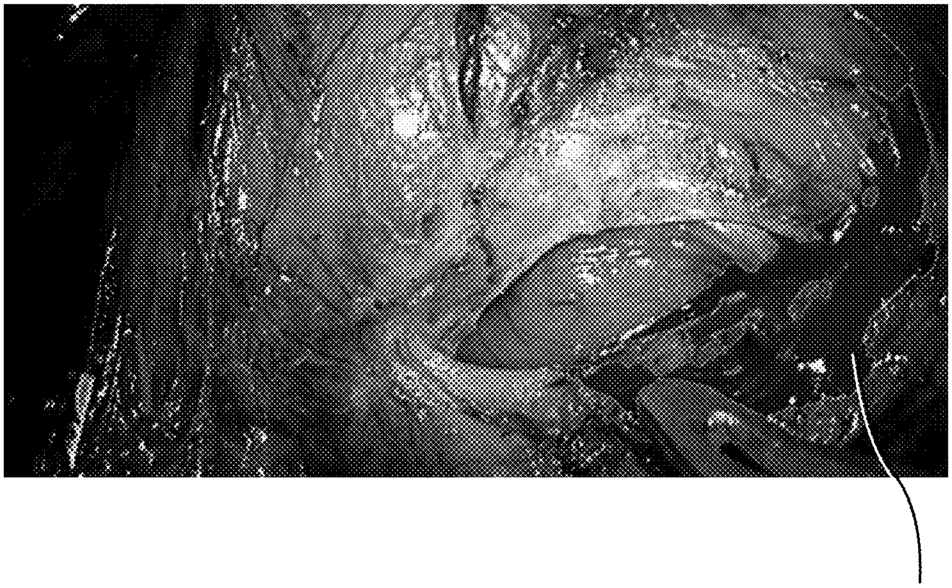
FIG. 17 is a view illustrating processing of an evaluation unit in the surgical content evaluation system according to the embodiment of the present invention.

FIG. 17 is a view illustrating processing of the evaluation unit in the surgical content evaluation system according to the embodiment of the present invention. As in the present embodiment, the analysis unit 12 compares the surgical image acquired by the acquisition unit 11 with the specific region analysis model stored in the storage unit 20, analyzes a specific region in the surgical image (a region formed by outflow of body fluids such as blood, bile, or intestinal fluid), and colors the specific region (a portion indicated by bleeding in the example shown in FIG. 17) and a contour of the specific region.

The evaluation unit 14 quantifies the number of times the specific region is analyzed by the analysis unit 12 (the number of times the body fluid has flowed out), and evaluates the contents of the surgery performed by the surgeon according to the number of times. The analysis unit 12 may identify the type of body fluid (blood, bile, intestinal fluid, etc.) forming the specific region. In this case, the evaluation unit 14 may evaluate the contents of the surgery performed by the surgeon according to the number of times for each type of body fluid forming the specific region. For example, when the analysis unit 12 identifies that the type of body fluid is blood, the evaluation unit 14 may gradually lower the evaluation as the number of times increases, and when the analysis unit 12 identifies that the type of body fluid is a specific body fluid (bile, intestinal fluid, or the like), once the outflow of the specific body fluid is analyzed, the evaluation may be significantly reduced.

Further, the analysis unit 12 analyzes a body fluid treatment tool (e.g., a gauze or the like for use in wiping bleeding) for processing a body fluid that has flowed out, as the instrument information. The evaluation unit 14 may evaluate the contents of the surgery performed by the surgeon according to the number of times the body fluid treatment tool is analyzed by the analysis unit 12 and the moving distance (the area per frame) of the body fluid treatment tool. When the number of times of insertion of a body fluid treatment tool (e.g., gauze or the like) or a moving distance is large, there is a possibility that treatment for bleeding is often performed. Therefore, the evaluation unit 14 may lower the evaluation as the number of times the body fluid treatment tool is analyzed or the value of the moving distance of the body fluid treatment tool increases.

The body fluid treatment tool (e.g., gauze) may be used to suppress the preserved tissue tenderly. Therefore, the evaluation unit 14 may correct the contents of the surgery using the anatomical structure of the body and the position information of the body fluid treatment tool. For example, when the preserved tissue and the body fluid treatment tool are close to each other so that the movement of the body fluid treatment tool is not analyzed (when it is estimated that the body fluid treatment tool is used to prevent the body fluid treatment tool from being protected), the evaluation unit 14 may not lower the evaluation even when the body fluid treatment tool is analyzed.

Figure 18:
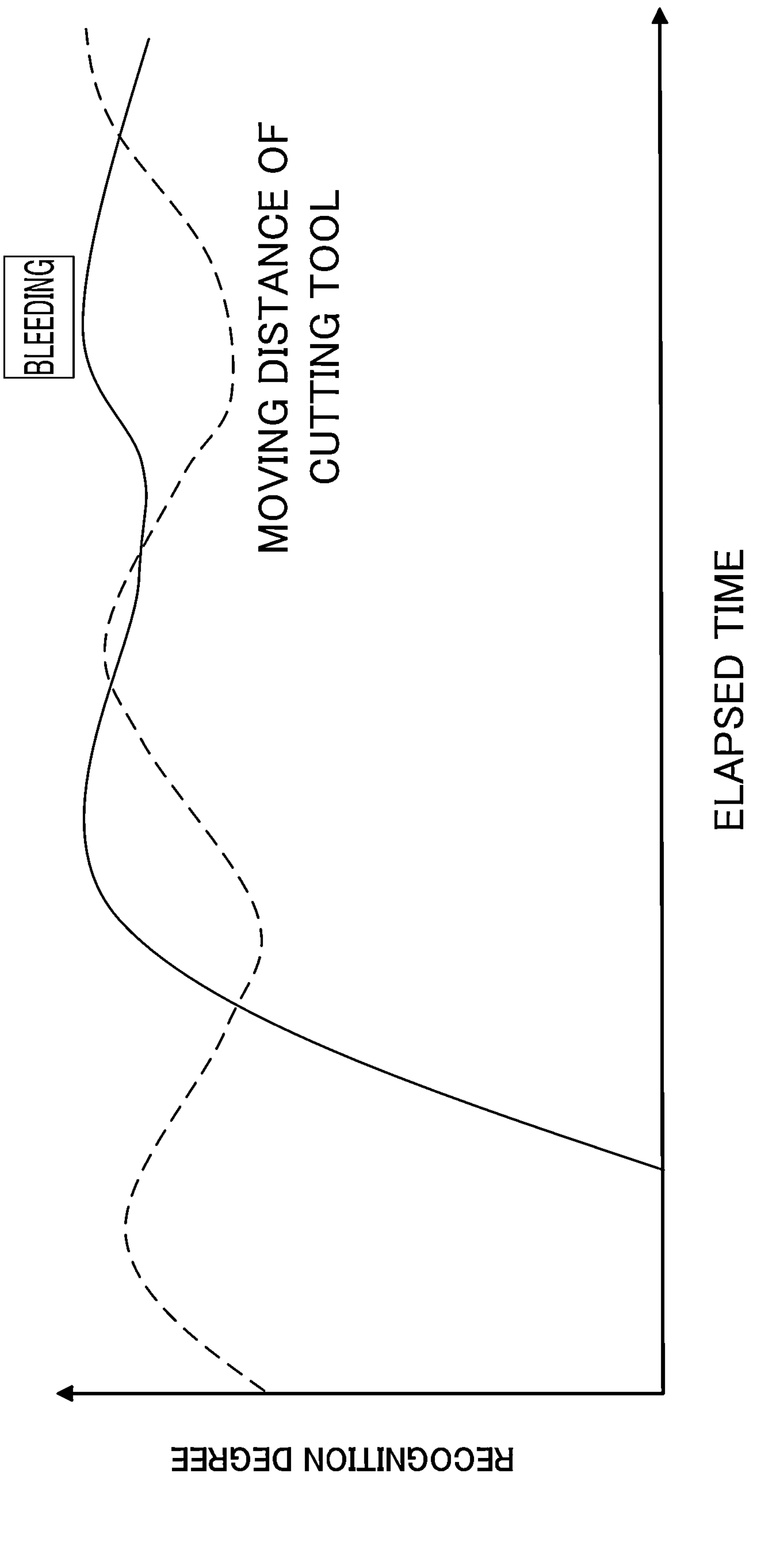
FIG. 18 is a diagram showing an example of evaluation criteria in the evaluation unit of the surgical content evaluation system according to the application example of the embodiment of the present invention.

FIG. 18 is a diagram showing an example of evaluation criteria in the evaluation unit of the surgical content evaluation system according to the application example of the embodiment of the present invention. FIG. 18 shows the temporal change in the area of a specific region (e.g., blood) and the moving distance of the instrument (e.g., cutting tool).

In the example shown in FIG. 18, the cutting tool continues to move without reducing the area of the specific region (without reducing the amount of bleeding). In such a case, it is estimated that the operation is proceeding without hemostasis. Therefore, the evaluation unit 14 lowers the evaluation.

Image Extraction and Moving Image Editing using Recognition Degree of Anatomical Structure As in the present embodiment, the surgical content evaluation system 1 may include an image editing unit that generates a digest image of the surgical image acquired by the acquisition unit 11. The image editing unit extracts, for example, a moving image of a predetermined time including a frame of each step in the surgery identified by the analysis unit 12 from the surgical images obtained by the acquisition unit 11 for each step, and combines these moving images to generate a digest image.

In such a case, the evaluation unit 14 identifies a surgical image (frame) in which the analysis unit 12 determines that the recognition degree with respect to information relating to a specific anatomical structure included in the body information is equal to or greater than a specific threshold.

Figure 19:
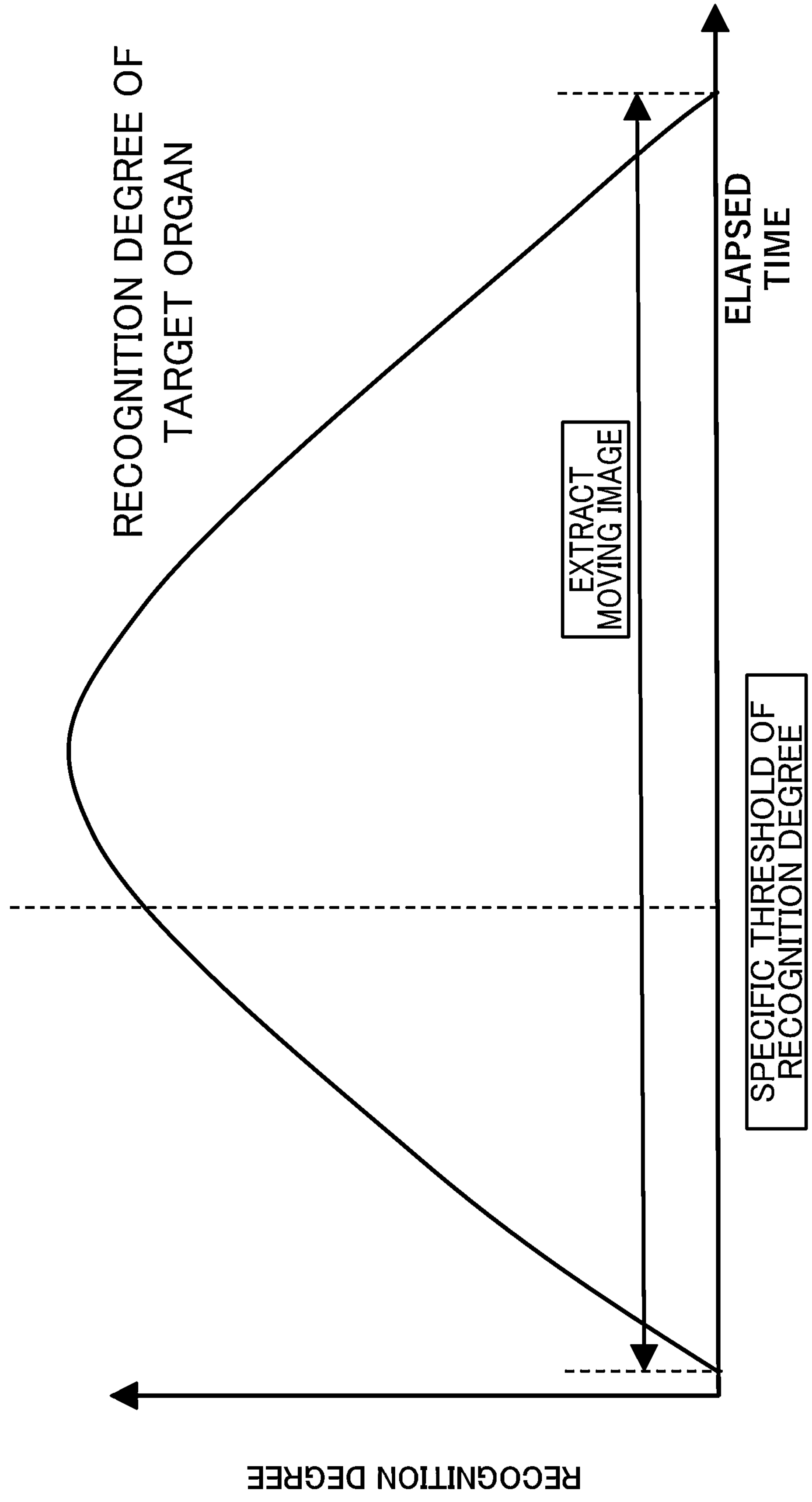
FIG. 19 is a diagram illustrating processing in an image editing unit of the surgical content evaluation system according to the application example of the embodiment of the present invention.

FIG. 19 is a diagram illustrating processing in the image editing unit of the surgical content evaluation system according to the application example of the embodiment of the present invention. FIG. 19 shows temporal changes in the recognition degree of the target organ and ranges of moving images to be extracted.

The evaluation unit 14 sets a surgical image (frame) in which the analysis unit 12 determines that the recognition degree with respect to information relating to a specific anatomical structure (e.g., a target organ such as nerve tissue) included in the body information is equal to or greater than a specific threshold (the area of the nerve tissue (the total amount of pixels or the confidence degree)) as a moving image extraction point. Then, the image editing unit automatically extracts a predetermined period before and after the moving image extraction point and edits the moving image. The predetermined period is, for example, a period from when the anatomical structure is analyzed by the analysis unit 12 (after the recognition degree of the anatomical structure is generated) until when the anatomical structure is no longer analyzed (until the recognition degree of the anatomical structure becomes 0).

The evaluation unit 14 may identify a surgical image (frame) with the confidence degree of the target organ being equal to or greater than a certain level. Further, the evaluation unit 14 may set the moving image extraction point based on the confidence degree of the operation tool and the structure or the graph of the area of the structure.

Thus, in the moving image obtained by imaging the entire surgery, the moving image extraction can be automatically performed from the point in time where the anatomical structure (e.g., nerve tissue) begins to appear to the point in time where the anatomical structure no longer appears. Thus, by evaluating the contents of the surgery using the moving image extracted from the specific scene during the surgery, the evaluation can be efficiently performed as compared with the case of evaluating the entire surgery based on the captured moving image.

In addition, for example, the image editing unit may display, in the extracted moving image, a trajectory (e.g., a cutting line or the like) of the instrument presented by the AI model which learns the cutting line of each expert doctor when the specific scene during the operation is extracted. Further, the image editing unit may display the predicted surgical field or the predicted structure after resection in the extracted moving image by Generative Adversarial Network (GAN) or the like.

Figure 20:
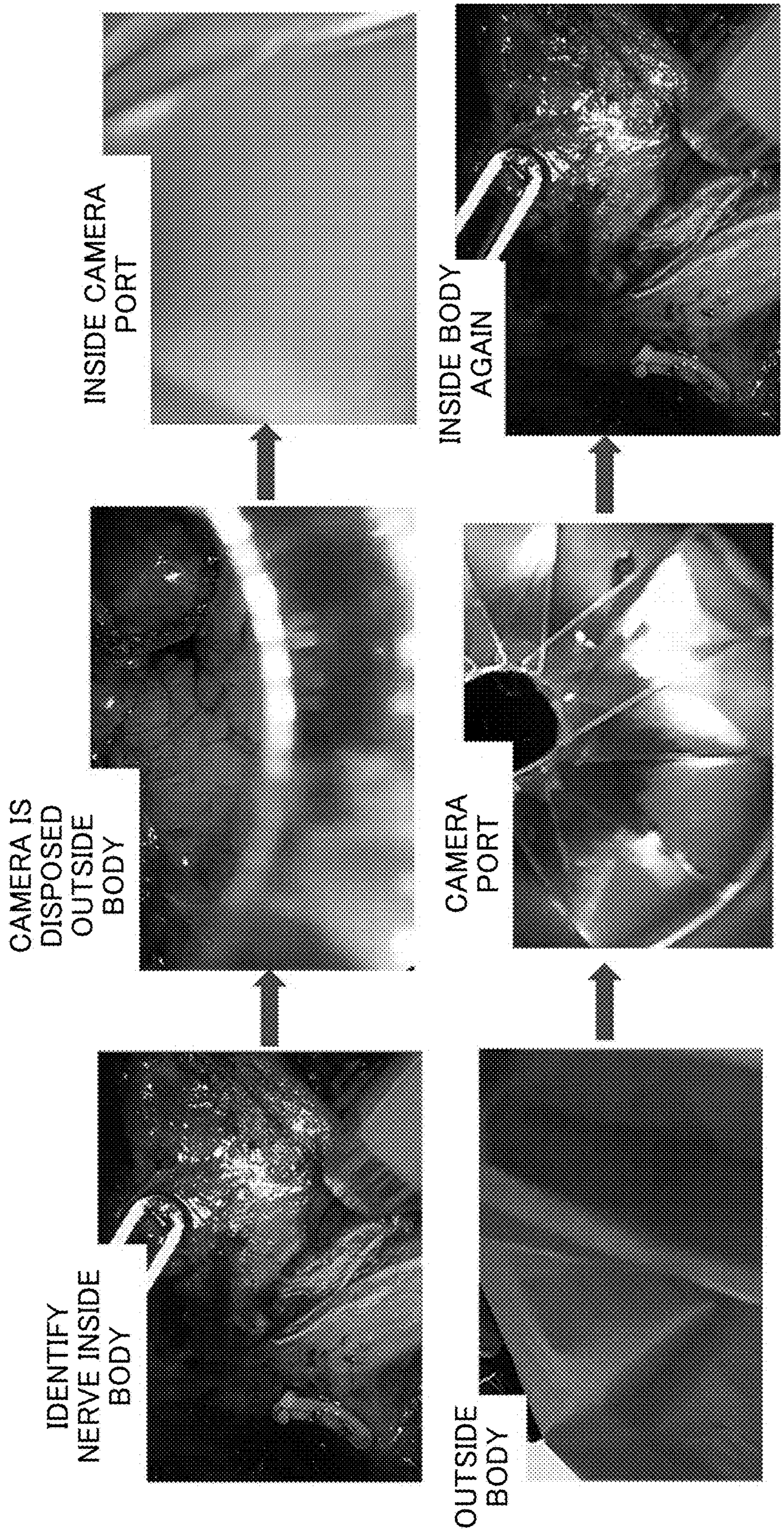
FIG. 20 provides views illustrating processing in the image editing unit of the surgical content evaluation system according to the application example of the embodiment of the present invention.

FIG. 20 provides views illustrating processing in the image editing unit of the surgical content evaluation system according to the application example of the embodiment of the present invention. FIG. 20 shows the transition of the surgical image by the operation of an imaging unit (e.g., a camera) for imaging the surgical image.

A camera that images the inside of the body is passed through a camera port inserted into the body from outside the body. The upper images of FIG. 20 show the transition of the surgical image when the camera disposed in the body is pulled out of the body. The lower images of FIG. 20 show the transition of the surgical image when the camera is inserted into the body from outside the body.

For example, when the camera is placed in the body and the structure is analyzed by the analysis unit 12, the confidence degree becomes zero when the camera is pulled out of the body. After that, when the camera is inserted from outside the body into the body, the structure is analyzed by the analysis unit 12 and the confidence degree increases. The evaluation unit 14 may identify a first point at which the confidence degree of the target organ becomes 0 and a second point at which the confidence degree increases again thereafter. Further, the analysis unit 12 may analyze a fixed structure (e.g., a camera port) outside the camera as the instrument information. In this case, the evaluation unit 14 may identify, as the first point, the time when such a structure is analyzed after the analysis of the body information is started. Based on the first point and the second point identified by the evaluation unit 14, the image editing unit may automatically delete the moving image between the first point and the second point.

According to the surgical content evaluation system 1 of this application example, it is possible to evaluate the content of the surgery performed by the surgeon according to the recognition degree indicating the degree of recognition of the body information in the surgical image.

For example, if the target organ or the like of the surgery is separated from the other organs and exposed, the physical information of the target organ or the like becomes clear in the surgical image, the degree of recognition of the physical information becomes higher, and the recognition degree becomes higher. On the other hand, when the target organ or the like of the surgery cannot be securely separated from other organs, the physical information of the target organ or the like becomes unclear in the surgical image, the degree of recognition of the physical information becomes lower, and the recognition degree becomes lower. As a matter of course, as the target organ or the like of the surgery is separated from the other organs and exposed more, the surgery to the target organ is performed more smoothly, the possibility of damage to the other organs is further reduced, and the surgery becomes a good surgery with less burden on the body of the patient (the evaluation of the contents of the surgery becomes higher).

Further, according to the surgical content evaluation system 1 of the application example, the analysis unit can calculate the recognition degree based on the confidence degree indicating the degree of confidence of the analysis result of the body information. Thus, from a more objective viewpoint, the recognition degree indicating the degree of recognition of the body information is calculated, and the contents of the surgery performed by the surgeon can be evaluated according to the recognition degree, so that the contents of the actual surgery can be evaluated more objectively.

Further, according to the surgical content evaluation system 1 of the application example, it is possible to evaluate the content of the surgery performed by the surgeon in accordance with a temporal change in the recognition degree.

For example, when the organ to be operated (body information to be analyzed) is a preserved organ, if the rate of increasing the recognition degree is fast, it is evaluated that the organ to be operated is exposed in a skilled manner. Further, when the target organ (body information to be analyzed) of the surgery is a resected organ, it is evaluated that the target organ is resected in a more skilled manner as the recognition degree transitions in a relatively low value. In addition, if the temporal change of the recognition degree with respect to a certain organ is relatively small, it is evaluated that there is no shake in the procedure. In these cases, the burden on the patient's body is low (the evaluation of the contents of the surgery becomes higher).

Further, according to the surgical content evaluation system 1 of the application example, it is possible to evaluate the difficulty level of the surgery in accordance with the information relating to the anatomical structure of the body included in the body information.

For example, in a case of gastric resection surgery, if the amount of fat, which is an example of an anatomical structure, is relatively small, the difficulty level in surgery is lowered because the blood vessel can be seen well; whereas, if the amount of fat, which is an example of an anatomical structure, is relatively large, the blood vessel is covered with fat, so that the blood vessel cannot be seen and adheres, so that the fat cannot be sufficiently lifted, so that the field of view is poor and the difficulty level in surgery increases.

Further, according to the surgical content evaluation system 1 of the application example, it is possible to evaluate the operation performance of the instrument in the surgery based on the trajectory of the distal end position of the instrument operated by the surgeon. As a result, since the accuracy of the trajectory analysis is improved and it is not necessary to recognize all the instruments, it is possible to suppress the load of the analysis processing.

Further, according to the surgical content evaluation system 1 of the application example, it is possible to evaluate the operation performance of the instrument in the surgery based on the positional relationship between the point of action which is a portion of the instrument being operated by the surgeon in contact with the anatomical structure and a portion of the anatomical structure in contact with the instrument.

In a case of resecting the anatomical structure, the appropriate tension is applied to the anatomical structure by the portion of the anatomical structure gripped by the forceps, and the cutting position is easily cut, or slack occurs in the anatomical structure and the cutting position is not clearly exposed. For example, when the tip (gripping portion) serving as the point of action of the forceps is located at a position where the surgeon appropriately grips the intended anatomical structure and applies moderate tension, the possibility that the organ to be resected can be resected without damaging the preserved organ is improved (a higher evaluation of the manner of operation of the instrument during surgery).

Further, according to the surgical content evaluation system 1 of the application example, among a plurality of surgical images continuously in a time series, it is possible to identify a surgical image having a recognition degree with respect to information relating to a specific anatomical structure included in body information that is determined to be equal to or greater than a specific threshold. This makes it possible to identify a point in time when a specific anatomical structure is exposed in a moving image composed of a plurality of surgical images continuously in a time series. For example, in a moving image, by attaching a marker to the identified point in time, a scene in which a specific anatomical structure is exposed can be quickly reproduced or edited based on the specified time point.

The present invention has been explained above using embodiments and application examples. However, it is needless to say that the technical scope of the present invention is not limited to the embodiments and the application examples described above. It is apparent to those skilled in the art that various changes and modifications can be made to the above-described embodiments and application examples. It is also apparent from the claims that embodiments to which such changes or improvements are added can be included in the technical scope of the present invention. In the above embodiments and application examples, the surgical content evaluation system has been described as a product invention of the present invention; however, the present invention can be regarded as a method executed by the surgical content evaluation system or a program for causing the surgical content evaluation system to function as various sections.

EXPLANATION OF REFERENCE NUMERALS

1 surgical content evaluation system
2 medical institution terminal
11 acquisition unit
12 analysis unit
13 time measurement unit
14 evaluation unit
15 transmission unit
20 storage unit

The invention claimed is:

1. A surgical content evaluation system for evaluating a content of surgery performed by a surgeon, the system comprising:
- an acquisition unit that acquires a surgical image, which is a captured image of a body of a patient on which the surgery is performed by the surgeon;
- an analysis unit that analyzes, in the surgical image, at least a difficulty of the surgery according to body information indicating a state of the body and/or instrument information indicating a state of an instrument operated by the surgeon; and
- an evaluation unit that evaluates at least one of an operational performance of the instrument, appropriateness of the surgery, or efficiency of the surgery with respect to the content of the surgery performed by the surgeon based on the body information and/or the instrument information analyzed by the analysis unit;

wherein
- the surgical image of the surgery includes a plurality of steps,
- the analysis unit analyzes each of the plurality of steps in the surgical image of the surgery including the plurality of steps,
- the surgical content evaluation system further includes a time measurement unit that measures an inter-step period of time, which is a period of time from one step of the plurality of steps to a next other step of the plurality of steps, and
- the evaluation unit evaluates a surgical skill for the one step of the plurality of steps, based on the inter-step period measured by the time measurement unit.

2. The surgical content evaluation system according to claim 1, wherein
- the analysis unit analyzes a specific region in the surgical image, and
- the evaluation unit evaluates, when the specific region in the surgical image has exceeded a predetermined threshold, that a body fluid has flowed out or an organ has been damaged.

3. The surgical content evaluation system according to claim 1, wherein
- the analysis unit analyzes the instrument information including information relating to the instrument, and
- the evaluation unit evaluates an operation performance of the instrument in the surgery based on the information relating to the instrument.

4. The surgical content evaluation system according to claims 1, wherein the analysis unit
- analyzes the body information including information relating to an anatomical structure of the body, and
- analyzes the body information and/or the instrument information including information relating to a position of the instrument with respect to the anatomical structure, and
- the evaluation unit evaluates an operation performance of the instrument with respect to the anatomical structure in the surgery based on the information relating to the position of the instrument with respect to the anatomical structure.

5. A method executed by a surgical content evaluation system for evaluating a content of surgery performed by a surgeon, the method comprising the steps of:
- acquiring a surgical image, which is a captured image of a body of a patient on which the surgery is performed by the surgeon;
- analyzing, in the surgical image, at least a difficulty of the surgery according to body information indicating a state of the body and/or instrument information indicating a state of an instrument operated by the surgeon;
- wherein the surgical image of the surgery includes a plurality of steps,
- analyzing each of the plurality of steps in the surgical image of the surgery including the plurality of steps,
- measuring an inter-step period of time, which is a period of time from one step of the plurality of steps to a next other step of the plurality of steps,
- evaluating a surgical skill for the one step of the plurality of steps, based on the inter-step period measured by the time measurement unit; and
- evaluating at least one of an operational performance of the instrument, appropriateness of the surgery, or efficiency of the surgery with respect to the content of the surgery performed by the surgeon based on the body information and/or the instrument information.

6. A surgical content evaluation system for evaluating a content of surgery performed by a surgeon, the system comprising:
- an acquisition unit that acquires a surgical image, which is a captured image of a body of a patient on which the surgery is performed by the surgeon;
- an analysis unit that analyzes, in the surgical image, at least a difficulty of the surgery according to body information indicating a state of the body; and
- an evaluation unit that evaluates at least one of quality of the surgery an operational performance of the instrument, appropriateness of the surgery, or efficiency of the surgery with respect to the content of the surgery performed by the surgeon based on the body information analyzed by the analysis unit;

wherein the surgical image of the surgery includes a plurality of steps, the analysis unit analyzes each of the plurality of steps in the surgical image of the surgery including the plurality of steps, the surgical content evaluation system further includes a time measurement unit that measures an inter-step period of time, which is a period of time from one step of the plurality of steps to a next other step of the plurality of steps, and the evaluation unit evaluates a surgical skill for the one step of the plurality of steps, based on the inter-step period measured by the time measurement unit.

7. The surgical content evaluation system according to claim 6, wherein the analysis unit calculates a recognition degree indicating a degree of recognition of the body information in the surgical image, and the evaluation unit evaluates the content of the surgery performed by the surgeon according to the recognition degree.

8. The surgical content evaluation system according to claim 7, wherein the analysis unit calculates a confidence degree indicating a degree of confidence of an analysis result of the body information, and calculates the recognition degree based on the confidence degree.

9. The surgical content evaluation system according to claim 7, wherein the evaluation unit evaluates the content of surgery performed by the surgeon according to a temporal change of the recognition degree.

10. The surgical content evaluation system according to claim 6, wherein the evaluation unit evaluates a difficulty level of surgery according to information relating to an anatomical structure of the body included in the body information.

11. The surgical content evaluation system according to claim 6, wherein the analysis unit analyzes a trajectory of a distal end position of an instrument operated by the surgeon, and the evaluation unit evaluates an operation performance of the instrument in the surgery based on the trajectory.

12. The surgical content evaluation system according to claim 6, wherein the analysis unit analyzes a positional relationship between a point of action, which is a portion of the instrument operated by the surgeon in contact with the anatomical structure, and a portion of the anatomical structure in contact with the instrument, and the evaluation unit evaluates the operation performance of the instrument in the surgery based on the positional relationship.

13. The surgical content evaluation system according to claim 7, wherein the acquisition unit acquires a plurality of surgical images continuously in a time series, and the evaluation unit identifies, among the plurality of surgical images, a surgical image having recognition degree with respect to information relating to a specific anatomical structure included in the body information that is determined to be equal to or greater than a specific threshold in the analysis unit.

14. The surgical content evaluation system according to claim 1, wherein the evaluation unit evaluates the surgical skill for the one step of the plurality of steps, based on the inter-step period measured by the time measurement unit as compared to a reference time stored in a table.

15. The surgical content evaluation system according to claim 1, wherein the analysis unit analyzes the body information and the instrument information including information relating to a position of the instrument with respect to the anatomical structure, the evaluation unit evaluates an operation performance of the instrument with respect to the anatomical structure in the surgery based on the information relating to the position of the instrument with respect to the anatomical structure, and the evaluation unit evaluates a surgical skill based on the operation performance of the instrument and based on the information relating to the position of the instrument with respect to the anatomical structure.

* * * * *